United States Patent [19]

Lacroix et al.

[11] Patent Number: 5,637,729
[45] Date of Patent: Jun. 10, 1997

[54] FUNGICIDAL 2-IMIDAZOLIN-5-ONES AND 2-IMIDAZOLINE-5-THIONES

[75] Inventors: Guy Lacroix, Lyons; Raymond Peignier, Caluire; Regis Pepin, Rillieux la Pape, all of France

[73] Assignee: Rhone-Poulenc Agrochimie, Lyon Cedex, France

[21] Appl. No.: 462,849

[22] Filed: Jun. 5, 1995

Related U.S. Application Data

[60] Division of Ser. No. 352,814, Dec. 1, 1994, which is a continuation-in-part of Ser. No. 993,700, Dec. 21, 1992, abandoned, and a continuation-in-part of PCT/FR93/00647, Jun. 29, 1993, and a continuation-in-part of Ser. No. 156, 647, Nov. 24, 1993, abandoned, and a continuation-in-part of Ser. No. 262,459, Jun. 20, 1994, abandoned.

[30] Foreign Application Priority Data

| Dec. 20, 1991 | [FR] | France | 91 16200 |
| Jul. 2, 1992 | [FR] | France | 92 08405 |
| Nov. 25, 1992 | [FR] | France | 92 14432 |
| Jun. 18, 1993 | [FR] | France | 93 07663 |
| Feb. 21, 1994 | [FR] | France | 94 02144 |

[51] Int. Cl.$^6$ .............. C07D 233/70; C07D 233/66; C07D 233/86; C07D 233/72; A01N 43/50
[52] U.S. Cl. .............. 548/316.7; 514/398; 548/317.1; 548/318.1; 546/274.4; 546/143; 546/171; 544/322; 544/405; 544/238
[58] Field of Search ............ 548/316.7; 546/278; 514/398

[56] References Cited

U.S. PATENT DOCUMENTS

| 3,513,187 | 5/1970 | Viennois | 260/471 |
| 4,097,578 | 6/1978 | Perronnet et al. | 548/317.1 |
| 4,237,131 | 12/1980 | Wootton et al. | 548/318.1 |
| 4,280,008 | 7/1981 | Schoellkopf et al. | 548/301 |
| 4,428,948 | 1/1984 | Miller et al. | 548/316.7 |
| 4,459,411 | 7/1984 | Wang | 548/317.1 |
| 4,547,517 | 10/1985 | Kühle et al. | 514/390 |
| 4,614,535 | 9/1986 | Schmierer et al. | 548/316.7 |
| 4,657,922 | 4/1987 | Rasmussen et al. | 548/318.1 |
| 4,692,532 | 9/1987 | Spivack et al. | 548/316.7 |
| 5,177,097 | 1/1993 | Poss | 548/317.1 |
| 5,213,607 | 5/1993 | Guaciaro | 548/316.7 |

FOREIGN PATENT DOCUMENTS

| 651021 | 7/1994 | Australia | 548/317.1 |
| 0121054 | 10/1984 | European Pat. Off. | 548/317.1 |
| 0283245 | 9/1988 | European Pat. Off. | 548/318.1 |
| 0303863 | 2/1989 | European Pat. Off. | 548/317.1 |
| 0367583 | 5/1990 | European Pat. Off. | 548/317.1 |
| 0494879 | 7/1992 | European Pat. Off. | 548/317.1 |
| 0551048 | 7/1993 | European Pat. Off. | 548/318.1 |
| 0599749 | 6/1994 | European Pat. Off. | 548/317.1 |
| 2329276 | 5/1977 | France | 548/317.1 |
| 1176660 | 8/1964 | Germany | 548/318.1 |
| 1258412 | 1/1968 | Germany | 548/317.1 |
| 2658941 | 7/1978 | Germany | 548/318.1 |
| 39-12937 | 7/1964 | Japan | 548/316.7 |
| 48-4784 | 2/1973 | Japan | 548/316.7 |
| 2-19363 | 1/1990 | Japan | 548/317.1 |
| 0169189 | 1/1969 | Sweden | 548/318.1 |
| 967166 | 8/1964 | United Kingdom | 548/317.1 |
| 967167 | 8/1964 | United Kingdom | 548/317.1 |
| 93/24467 | 12/1993 | WIPO | 548/317.1 |
| 94/01410 | 1/1994 | WIPO | 548/317.1 |

OTHER PUBLICATIONS

"Dictionary of Organic Compounds," 5th ed., vol. 2, p. 2058, Chapman and Hall, New York, US (1988).
"Dictionary of Organic Compounds," 5th ed., vol. 3, p. 2148, Chapman and Hall, New York, US (1988).
"Dictionary of Organic Compounds," 5th ed., vol. 3, p. 2676, Chapman and Hall, New York, US (1988).
"Dictionary of Organic Compounds," 5th ed., vol. 4, pp. 3723–3724, Chapman and Hall, New York, US (1988).
"Dictionary of Organic Compounds," 5th ed., vol. 4, p. 3890, Chapman and Hall, New York, US (1988).
Dr. O.-A. Neumüller, "Römpps Chemie–Lexikon," pp. 1805–1806, Franckh'sche Verlagshandlung, Stuttgart, DE (1984).
Chemical Abstracts, vol. 113, No. 5, Jul. 30, 1990, p. 390, col. 2, abstract No. 46760c, Columbus, Ohio, U.S.
Chemical Abstracts, vol. 113, No. 11, Sep. 10, 1990, abstract No. 97563y (Mishra et al).
Chemical Abstracts, vol. 116, No. 25, Jun. 22, 1992, abstract No. 255536k (Kadry et al).
Chemical Abstracts, vol. 115, No. 5, Aug. 5, 1991, abstract No. 49535k (Ismail et al).
Chemical Abstracts, vol. 97, No. 3, Jul. 19, 1982, abstract No. 23687w (Badr et al).
Chemical Abstracts, vol. 118, No. 7, Feb. 15, 1993, abstract No. 59637w (Trivedi et al).
Yamamoto et al, Journal of the Chemical Society, Perkin Transactions 1, 1990, pp. 3003–3009.
Chemical Abstracts, vol. 108, No. 9, Feb. 29, 1988, abstract No. 75264w and Cas Registry 1987 Supplement, RN: 110315–05–4.
Chemical Abstracts, vol. 98, No. 13, Mar. 28, 1993, abstract No. 107198w, Cas Registry 1981 Supplement, RN: 79402–65–6, 79402–67–8, 79402–73–6 and Padwa et al, J. Org. Chem., vol. 48, No. 5, 1983, pp. 695–703.
Chemical Abstracts, vol. 85, No. 15, Oct. 11, 1976, abstract No. 108496k and Cas Registry 1976 Supplement, RN: 60272–65–3, 60272–66–4.
Chemical Abstracts, vol. 83, No. 5, Aug. 4, 1975, abstract No. 43702m and Cas Registry 1975 Supplement, RN: 56159–78–5.
Chemical Abstracts, vol. 95, No. 19, Nov. 9, 1981, abstract No. 169042n and Cas Registry 1965–1971, RN: 4855–22–5, 4855–25–8.
Cas Registry 1965–1971, RN: 4892–65–3, 4892–66–4 (1995).
Cas Registry 1965–1971, RN: 4855–22–5, 4855–23–6, 4855–24–7, 4855–25–8, 4855–26–9, 4855–27–0 (1995).

Primary Examiner—Floyd D. Higel
Attorney, Agent, or Firm—Burns, Doane, Swecker & Mathis, L.L.P.

[57] ABSTRACT

Fungicidal 2-imidazolin-5-ones and 2-imidazoline-5-thiones, processes for their preparation, fungicidal compositions containing them and methods of using them to treat or prevent fungal disease in crops.

3 Claims, No Drawings

FUNGICIDAL 2-IMIDAZOLIN-5-ONES AND 2-IMIDAZOLINE-5-THIONES

CROSS-REFERENCE TO RELATED APPLICATIONS

This is a division of application Ser. No. 08/352,814, filed Dec. 1, 1994, pending which is a continuation-in-part of earlier U.S. application Ser. No. 07/993,700, filed Dec. 21, 1992; now abandoned International Patent Application No. PCT/FR93/00647, filed Jun. 29, 1993 and designating the United States; U.S. application Ser. No. 08/156,647, filed Nov. 24, 1993; now abandoned and U.S. application Ser. No. 08/262,459, filed Jun. 20, 1994; now abandoned all of which are incorporated by reference herein in their entireties and relied upon.

The present invention relates to novel fungicidal imidazolinone and imidazolinethione compounds for use in plant protection. It also relates to the processes for the preparation of said compounds and to the compounds which can optionally be used as intermediates in the preparation processes. It further relates to the use of these compounds as fungicides, to fungicidal compositions comprising these compounds and to methods for combating fungal diseases in crops using these compounds.

One object of the present invention is to provide compounds showing improved properties in the treatment of fungal diseases.

Another object of the present invention is to provide compounds showing a spectrum of use in the field of fungal diseases which is also improved.

In a first major aspect of the present invention, it has been found that these objects can be achieved by virtue of compounds of the invention which are 2-imidazolin-5-one and 2-imidazoline-5-thione derivatives of the general formula (I):

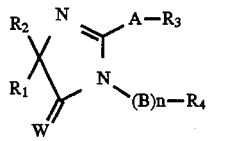

wherein:

W is a sulfur or oxygen atom or an S═O group;
A represents O or S;
n=0 or 1;
B represents NR$_5$ or O or S or CR$_5$R$_6$ or SO$_2$ or C═O;
R$_1$ and R$_2$, which are identical or different, represent:
  H, provided that one of the two groups is different from H;
  an alkyl or haloalkyl radical having 1 to 6 carbon atoms;
  an alkoxyalkyl, alkylthioalkyl, alkylsulfonylalkyl, monoalkylaminoalkyl, alkenyl or alkynyl radical having 2 to 6 carbon atoms;
  a dialkylaminoalkyl or cycloalkyl radical having 3 to 7 carbon atoms;
  an aryl radical comprising phenyl, naphthyl, thienyl, furyl, pyridyl, benzothienyl, benzofuryl, quinolyl, isoquinolyl or methylenedioxyphenyl, optionally substituted by 1 to 3 groups chosen from R$_7$; or
  an arylalkyl, aryloxyalkyl, arylthioalkyl or alkylsulfonylalkyl radical, the terms aryl and alkyl having the definitions given above;
  or R$_1$ and R$_2$ can form, with the carbon to which they are bonded on the ring, a carbocycle or a heterocycle having from 5 to 7 atoms, it being possible for these rings to be fused to a phenyl, optionally substituted by 1 to 3 groups chosen from R$_7$;
R$_3$ represents:
  an alkyl group having 1 to 6 carbon atoms;
  an alkoxyalkyl, alkylthioalkyl, alkylsulfonylalkyl, haloalkyl, cyanoalkyl, thiocyanatoalkyl, oxoalkyl, alkenyl or alkynyl group having 2 to 6 carbon atoms;
  a dialkylaminoalkyl, alkoxycarbonylalkyl or N-alkylcarbamaoylalkyl group having 3 to 6 carbon atoms;
  a N,N-dialkylcarbamoylalkyl group having 4 to 8 carbons atoms; or
  an arylalkyl group, the alkyl part being a radical having 1 to 6 carbon atoms and the aryl part being phenyl, naphthyl, thienyl, furyl or pyridyl, optionally substituted by 1 to 3 groups chosen from R$_7$;
R$_4$ represents:
  a hydrogen atom (when n is equal to 1);
  an alkyl group having 1 to 6 carbon atoms;
  an alkoxyalkyl, alkylthioalkyl, haloalkyl, cyanoalkyl, thiocyanatoalkyl, alkenyl or alkynyl group having 2 to 6 carbon atoms;
  a dialkylaminoalkyl, alkoxycarbonylalkyl or N-alkylcarbamoylalkyl group having 3 to 6 carbon atoms;
  a N,N-dialkylcarbamoylalkyl group having 4 to 8 carbon atoms;
  an aryl radical, comprising phenyl, naphthyl, thienyl, furyl, pyridyl, pyrimidyl, pyridazinyl, pyrazinyl, benzothienyl, benzofuryl, quinolyl, isoquinolyl or methylenedioxyphenyl, optionally substituted by 1 to 3 groups chosen from R$_7$;
  an arylalkyl, aryloxyalkyl, arylthioalkyl or arylsulfonylalkyl radical, the terms aryl and alkyl having the definitions given above;
  an amino group disubstituted by two identical or different groups chosen from:
    an alkyl radical having 1 to 6 carbon atoms;
    an alkoxyalkyl, alkenyl or alkynyl radical having 3 to 6 carbon atoms;
    a cycloalkyl radical having 3 to 7 carbon atoms;
    an arylalkyl, such as defined above, phenyl or naphthyl radical, optionally substituted by 1 to 3 groups chosen from R$_7$; and
    a thienylmethyl or furfuryl radical; or
  a pyrrolidino, piperidino, morpholino or piperazino group, optionally substituted by aryl having 1 to 3 carbon atoms;
R$_5$ represents:
  H, except when R$_4$ is H;
  an alkyl, haloalkyl, alkylsulfonyl or haloalkylsulfonyl radical having 1 to 6 carbon atoms;
  an alkoxyalkyl, alkylthioalkyl, acyl, alkenyl, alkynyl, haloacyl, alkoxycarbonyl, haloalkoxycarbonyl, alkoxyalkylsulfonyl or cyanoalkylsulfonyl radical having 2 to 6 carbon atoms;
  an alkoxyalkoxycarbonyl, alkylthioalkoxycarbonyl or cyanoalkoxycarbonyl radical having 3 to 6 carbon atoms;
  a formyl radical;
  a cycloalkyl, alkoxyacyl, alkylthioacyl, cyanoacyl, alkenylcarbonyl or alkynylcarbonyl radical having 3 to 6 carbon atoms;
  a cycloalkylcarbonyl radical having 4 to 8 carbon atoms;
  a phenyl; arylalkylcarbonyl, especially phenylacetyl or phenylpropionyl; arylcarbonyl, especially benzoyl, optionally substituted by 1 to 3 groups chosen from
R₇; thienylcarbonyl; furylcarbonyl; pyridylcarbonyl;
benzyloxycarbonyl; furfuryloxycarbonyl; tetrahydrofurfuryloxycarbonyl; thienylmethoxycarbonyl;
pyridylmethoxycarbonyl; phenoxycarbonyl or
(phenylthio)carbonyl, the phenyl being itself optionally substituted by 1 to 3 groups chosen from R₇;
(alkylthio)carbonyl; (haloalkylthio)carbonyl;
(alkoxyalkylthio)carbonyl; (cyanoalkylthio)
carbonyl; benzylthio)carbonyl; (furfurylthio)
carbonyl; (tetrahydrofurfurylthio)carbonyl;
(thienylmethylthio)carbonyl; (pyridylmethylthio)
carbonyl; or arylsulfonyl radical;
a carbamoyl radical, optionally mono- or disubstituted
by:
  an alkyl or haloalkyl group having 1 to 6 carbon atoms;
  a cycloalkyl, alkenyl or alkynyl group having 3 to 6 carbon atoms;
  an alkoxyalkyl, alkylthioalkyl or cyanoalkyl group having 2 to 6 carbon atoms; or
  a phenyl, optionally substituted by 1 to 3 R₇ groups;
a sulfamoyl group, optionally mono- or disubstituted
by:
  an alkyl or haloalkyl group having 1 to 6 carbon atoms;
  a cycloalkyl, alkenyl or alkynyl group having 3 to 6 carbon atoms;
  an alkoxyalkyl, alkylthioalkyl or cyanoalkyl group having 2 to 6 carbon atoms; or
  a phenyl, optionally substituted by 1 to 3 R₇ groups; or
an alkylthioalkylsulfonyl group having 3 to 8 carbon atoms or a cycloalkylsulfonyl group having 3 to 7 carbon atoms;

R₆ represents:
  a hydrogen atom;
  a cyano group;
  an alkyl group having 1 to 6 carbon atoms or a cycloalkyl group having 3 to 7 carbon atoms;
  an acyl or alkoxycarbonyl group having 2 to 6 carbon atoms; or
  a benzoyl group, optionally substituted by 1 to 3 R₇ groups; and R₇ represents:
  a halogen atom;
  an alkyl, haloalkyl, alkoxy, haloalkoxy, alkylthio, haloalkylthio or alkylsulfonyl radical having 1 to 6 carbon atoms;
  a cycloalkyl, halocycloalkyl, alkenyloxy, alkynyloxy, alkenylthio or alkynylthio radical having 3 to 6 carbon atoms;
  a nitro or cyano group;
  an amino radical, optionally mono- or disubstituted by an alkyl or acyl radical having 1 to 6 carbon atoms or an alkoxycarbonyl radical having 2 to 6 carbon atoms; or
  a phenyl, phenoxy or pyridyloxy radical, these radicals optionally being substituted;

and the corresponding agriculturally acceptable salts.

Certain specific compounds of the formula (I), having the formula (Ia):

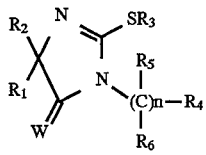

wherein W, R₁ to R₆ and n have the same meaning as in formula (I), are known. Denoted S-alkylated derivatives of 5,5-diphenyl-2-thiohydantoin and of 5,5-diphenyldithiohydrantoin, those particular compounds have been especially studied for their pharmacological properties, as described in:

(a) Zejc, A., *Dissertationes Pharmaceuticae et pharmacologicae*, Warsaw, 20 (5), 507–524 and 525–537 (1968);

(b) Lucka-Sobstel, B. and Zejc, A., *Dissertaniones Pharmaceuticae et pharmacologicae*, 22 (1), 13–19 (1970); and (c) Fetter, J., Harsanyi, K., Nyitrai, J. and Lempert, K., *Acta Chemica* (Budapest), 78 (3), 325–333 (1973).

No agricultural fungicidal activity has been previously described for these compounds.

Other specific compounds of formula (I) have been described by (d) Böhme, Martin and Strahl in *Archiv der Pharmazie*, 313, 10–15 (1980). They are the three compounds of the formula:

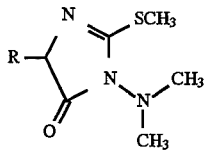

wherein R is H, CH₃ or phenyl. These compounds are thus included in the compounds of formula (Ib), which form part of the invention:

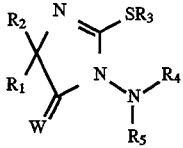

wherein W and R₁ to R₅ have the same meaning as in formula (I) above.

In this first major aspect of the invention, the compounds which are preferred for their better fungicidal activity and/or their ease of synthesis are:

(1) the compounds of formula (Ib);
(2) the compounds of formula (I), in particular those of formula (Ib), in which R₅ is a hydrogen atom;
(3) the compounds in which R₁ and R₂ are different from H;
(4) the compounds in which R₂ represents an alkyl group having 1 to 3 carbon atoms;
(5) the compounds in which R₁ represents a phenyl ring, optionally substituted by R₇;
(6) the compounds in which R₃ represents an alkyl group having 1 to 3 carbon atoms;
(7) the compounds in which R₄ represents a phenyl ring, optionally substituted by R₇; and
(8) the compounds in which R₃ represents a methyl group.

In a second major aspect of the present invention, the objects of the invention noted hereinabove can be achieved by virtue of compounds of the invention which are 2-imidazolin-5-one and 2-imidazoline-5-thione derivatives of the general formula (I'):

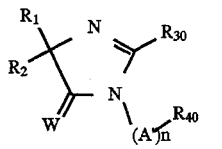

wherein:
W is a sulfur or oxygen atom or an S=O group, as defined with formula (I) hereinabove;
n=0 or 1, as defined with formula (I) hereinabove;
A' represents $NR_5$ or O or S or $CR_5R_6$ or $SO_2$ or C=O;
$R_1$ and $R_2$, which are identical or different, and which are as defined with formula (I) above, represent:
  H, provided that one of the two groups is different from H;
  an alkyl or haloalkyl radical having 1 to 6 carbon atoms;
  an alkoxyalkyl, alkylthioalkyl, alkylsulfonylalkyl, monoalkylaminoalkyl, alkenyl or alkynyl radical having 2 to 6 carbon atoms;
  a dialkylaminoalkyl or cycloalkyl radical having 3 to 7 carbon atoms;
  an aryl radical comprising phenyl, naphthyl, thienyl, furyl, pyridyl, benzothienyl, benzofuryl, quinolyl, isoquinolyl or methylenedioxyphenyl, optionally substituted by 1 to 3 groups chosen from $R_7$; or
  an arylalkyl, aryloxyalkyl, arylthioalkyl or arylsulfonylalkyl radical, the terms aryl and alkyl having the definitions given above in connection with formula (I');
or $R_1$ and $R_2$ can form, with the carbon to which they are bonded on the ring, a carbocycle or a heterocycle having from 5 to 7 atoms, it being possible for these rings to be fused to a phenyl, optionally substituted by 1 to 3 groups chosen from $R_7$;
$R_{30}$ represents:
  a hydrogen atom or an alkyl group having 1 to 6 carbon atoms;
  an alkoxyalkyl, alkylthioalkyl, alkylsulfonylalkyl, haloalkyl, cyanoalkyl, thiocyanatoalkyl, oxoalkyl, alkenyl or alkynyl group having 2 to 6 carbon atoms;
  a dialkylaminoalkyl, alkoxycarbonylalkyl or N-alkylcarbamoylalkyl group having 3 to 6 carbon atoms; or
  an N,N-dialkylcarbamoylalkyl group having 4 to 8 carbon atoms;
$R_{40}$ represents:
  a hydrogen atom (when n is equal to 1);
  an alkyl group having 1 to 6 carbon atom;
  an alkoxyalkyl, alkylthioalkyl, haloalkyl, cyanoalkyl, thiocyanatoalkyl, alkenyl or alkynyl group having 2 to 6 carbon atoms;
  a dialkylaminoalkyl, alkoxycarbonylalkyl or N-alkylcarbamoylalkyl group having 3 to 6 carbon atoms;
  an N,N-dialkylcarbamoylalkyl group having 4 to 8 carbon atom;
  an aryl radial, comprising phenyl, naphthyl, thienyl, furyl, pyridyl, imidazolyl, pyrazolyl, pyrrolyl, triazolyl, pyrimidyl, pyridazinyl, pyrazinyl, benzothienyl, benzofuryl, quinolyl, isoquinolyl or methylenedioxyphenyl, optionally substituted by 1 to 3 groups chosen from $R_7$;
  an arylalkyl, aryloxyalkyl, arylthioalkyl or arylsulfonylalkyl radical, the terms aryl and alkyl having the definitions given above with respect to formula (I');
  an amino group disubstituted by two identical or different groups chosen from:
    an alkyl radical having 1 to 6 carbon atom;
    an alkoxyalkyl, alkenyl or alkynyl radical having 3 to 6 carbon atoms;
    a cycloalkyl radical having 3 to 7 carbon atoms;
    an arylalkyl, such as defined above with respect to formula (I'), phenyl or naphthyl radical, optionally substituted by 1 to 3 groups chosen from $R_7$; and
    a thienylmethyl or furfuryl radical; or
  a pyrrolidino, piperidino, morpholino or piperazino group, optionally substituted by alkyl having 1 to 3 carbon atoms;
$R_5$ is as defined with formula (I) above and represents:
  H, except when $R_{40}$ is H;
  an alkyl, haloalkyl, alkylsulfonyl or haloalkylsulfonyl radical having 1 to 6 carbon atoms;
  an alkoxyalkyl, alkylthioalkyl, acyl, alkenyl, alkynyl, haloacyl, alkoxycarbonyl, haloalkoxycarbonyl, alkoxyalkylsulfonyl or cyanoalkylsulfonyl radical having 2 to 6 carbon atoms;
  an alkoxyalkoxycarbonyl, alkylthioalkoxycarbonyl or cyanoalkoxycarbonyl radical having 3 to 6 carbon atoms;
  a formyl radical;
  a cycloalkyl, alkoxyacyl, alkylthioacyl, cyanoacyl, alkenylcarbonyl or alkynylcarbonyl radical having 3 to 6 carbon atoms;
  a cycloalkylcarbonyl radical having 4 to 8 carbon atoms;
  a phenyl; arylalkylcarbonyl, especially phenylacetyl or phenylpropionyl; arylcarbonyl, especially benzoyl, optionally substituted by 1 to 3 groups chosen from $R_7$; thienylcarbonyl; furylcarbonyl; pyridylcarbonyl; benzyloxycarbonyl; furfuryloxycarbonyl; tetrahydrofurfuryloxycarbonyl; thienylmethoxycarbonyl; pyridylmethoxycarbonyl; phenoxycarbonyl or (phenylthio)carbonyl, the phenyl being itself optionally substituted by 1 to 3 groups chosen from $R_7$; (alkylthio)carbonyl; (haloalkylthio)carbonyl; (alkoxyalkylthio)carbonyl; (cyanoalkylthio)carbonyl; (benzylthio)carbonyl; (furfurylthio)carbonyl; (tetrahydrofurfurylthio)carbonyl; (thienylmethylthio)carbonyl; (pyridylmethylthio)carbonyl; or arylsulfonyl radical; or
  a carbamoyl radical, optionally mono- or disubstituted by:
    an alkyl or haloalkyl group having 1 to 6 carbon atom;
    a cycloalkyl, alkenyl or alkynyl group having 3 to 6 carbon atoms;
    an alkoxyalkyl, alkylthioalkyl or cyanoalkyl group having 2 to 6 carbon atoms; or
    a phenyl, optionally substituted by 1 to 3 $R_7$ groups;
  a sulfamoyl group, optionally mono- or disubstituted by:
    an alkyl or haloalkyl group having 1 to 6 carbon atoms;
    a cycloalkyl, alkenyl or alkynyl group having 3 to 6 carbon atoms;
    an alkoxyalkyl, alkylthioalkyl or cyanoalkyl group having 2 to 6 carbon atoms; or
    a phenyl, optionally substituted by 1 to 3 $R_7$ groups; or an alkylthioalkylsulfonyl group having 3 to 8 carbon atoms or a cycloalkylsulfonyl group having 3 to 7 carbon atoms;

$R_6$ is as defined with formula (I) above and represents:
a hydrogen atom;
a cyano group;
an alkyl group having 1 to 6 carbon atoms or a cycloalkyl group having 3 to 7 carbon atoms;
an acyl or alkoxycarbonyl group having 2 to 6 carbon atoms; or
a benzoyl group, optionally substituted by 1 to 3 $R_7$ groups; and $R_7$ is as defined with formula (I) above and represents:
a halogen atom;
an alkyl, haloalkyl, alkoxy, haloalkoxy, alkylthio, haloalkylthio or alkylsulfonyl radical having 1 to 6 carbon atoms;
a cycloalkyl, halocycloalkyl, alkenyloxy, alkynyloxy, alkenylthio or alkynylthio radical having 3 to 6 carbon atoms;
a nitro or cyano group;
an amino radical, optionally mono- or disubstituted by an alkyl or acyl radical having 1 to 6 carbon atoms or an alkoxycarbonyl radical having 2 to 6 carbon atoms; or
a phenyl, phenoxy or pyridyloxy radical, these radicals optionally being substituted;
and the corresponding agriculturally acceptable salts and the optically active isomers;
with the proviso that when n=0, $R_{40}$ is other than an optically active residue, deriving from an optically active primary amine or from an optically active amino acid.

Certain compounds belonging to the family of the 2-imidazolin-5-ones of general formulae:

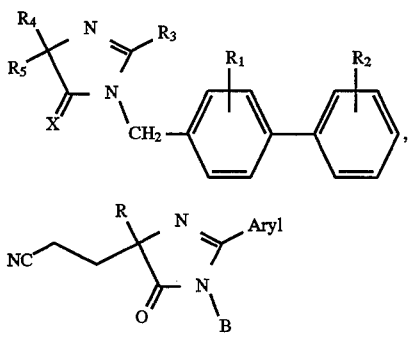

are known for their herbicidal properties from the documents of European Patents 41623, 41624, 215738, 226947, 261705, 303863, 433655 and 436483 and Patents U.S. Pat. No. 4,925,944, DE 3913757, GB 2167062, GB 2192877 and JP 3196570.

The imidazolinones of the formulae:

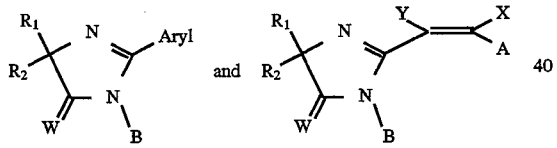

and

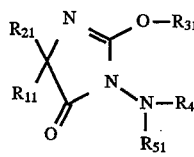

have been described for their pharmaceutical properties by published applications WO 9114679, JP 8055467 and DE 1176660 and 1258412, respectively. No agricultural fungicidal activity has been described for compounds of formula (I').

The compounds of formula (I'a):

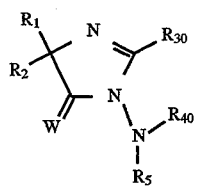

wherein $R_1$, $R_2$, $R_{30}$, $R_{40}$, $R_5$ and W are as defined with formula (I') are novel.

In this second major aspect of the invention, the compounds which are preferred for their better fungicidal activity and/or for their ease of synthesis are:

(1) the compounds of formula (I'a);
(2) the compounds of formula (I'), in particular those of formula (I'a), in which $R_5$ is a hydrogen atom;
(3) the compounds in which $R_1$ and $R_2$ are other than H;
(4) the compounds in which $R_2$ represents an alkyl group having 1 to 3 carbon atoms, preferably methyl;
(5) the compounds in which $R_1$ represents the phenyl ring, optionally substituted by $R_7$;
(6) the compounds in which $R_{30}$ represents a hydrogen atom or an alkyl group having 1 to 3 carbon atoms, optionally substituted by one or more halogens, methoxy or methylthio;
(7) the compounds in which $R_{40}$ represents the phenyl ring, optionally substituted by $R_7$; and
(8) the compounds of formula (I') in which W represents an oxygen atom.

In a third major aspect of the present invention, the objects of the invention noted hereinabove can be achieved in whole or in part as a result of compounds of the invention which are derivatives of 2-alkoxy-2-imidazolin-5-ones of the general formula (I"):

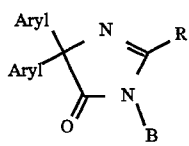

wherein:
$R_{11}$ represents an aryl or heteroaryl radical having 1 or 2 rings and from 5 to 10 ring atoms, from 0 to 3 of the ring atoms being heteroatoms, which can be the same or different, selected from the group consisting of N, O and S, at least one ring being aromatic or heteroaromatic, said aryl or heteroaryl radical being optionally substituted by from 1 to 3 $R_{61}$ groups, which can be the same or different ($R_{11}$ preferably being phenyl, naphthyl, thienyl, furyl, pyridyl, benzothienyl, benzofuryl, quinolinyl, isoquinolinyl or methylenedioxyphenyl, each of these radicals being optionally substituted by from 1 to 3 groups selected from among the meanings of $R_{61}$);

$R_{21}$ represents an alkyl or haloalkyl radical having from 1 to 3 carbon atoms, the haloalkyl radical having 1 or more halogen atoms as substituents;

or $R_{11}$ and $R_{21}$ form, together with the ring carbon atom to which they are bonded, a carbocyclic or heterocyclic ring having from 5 to 7 atoms and from 0 to 3 hetero ring atoms, which can be the same or different, selected from the group consisting of N, O and S, said ring being optionally fused to a benzene ring, the ring system being optionally substituted by from 1 to 3 $R_{61}$ groups, which can be the same or different;

$R_{31}$ represents an alkyl or haloalkyl radical having from 1 to 3 carbon atoms, the haloalkyl radical being substituted by 1 or more halogen atoms;

$R_{41}$ represents an aryl or heteroaryl radical having 1 or 2 rings and from 5 to 10 ring atoms, from 0 to 3 of the ring atoms being heteroatoms, which can be the same or different, selected from the group consisting of N, O and S, at least one ring being aromatic or heteroaromatic, said aryl or heteroaryl radical being optionally substituted by from 1 to 3 $R_{61}$ groups, which can be the same or different ($R_{41}$ preferably being phenyl, naphthyl, pyridyl, pyrimidyl, pyridazinyl, pyrazinyl, benzothienyl, benzofuryl, quinolinyl, isoquinolinyl or methylenedioxyphenyl, each of these radicals being optionally substituted by from 1 to 3 groups selected from among the meanings of $R_{61}$);

$R_{51}$ represents hydrogen, formyl, acyl having from 2 to 6 carbon atoms, aroyl, alkoxycarbonyl having from 2 to 6 carbon atoms, aryloxycarbonyl, alkylsulfonyl having from 1 to 6 carbon atoms or arylsulfonyl, the aryl portion of the aroyl, aryloxycarbonyl and arylsulfonyl radicals having from 6 to 10 carbon atoms and being optionally substituted by from 1 to 3 $R_{61}$ groups, which can be the same or different; and $R_{61}$ represents:
a halogen atom;
an alkyl, haloalkyl, cyanoalkyl, alkoxy, haloalkoxy, cyanoalkoxy, alkylthio, haloalkylthio, cyanoalkylthio or alkylsulfonyl radical having from 1 to 6 carbon atoms, the haloalkyl, haloalkoxy and haloalkylthio radicals bearing 1 or more halogen atoms as substituents;
a cycloalkyl, halocycloalkyl, alkenyl, alkynyl, alkenyloxy, alkynyloxy, alkenylthio or alkynylthio radical having from 3 to 6 carbon atoms, the halocycloalkyl radical bearing 1 or more halogen atoms as substituents;
a nitro, cyano or thiocyanato group;
an amino radical optionally mono- or disubstituted by an alkyl or acyl radical having from 1 to 6 carbon atoms or an alkoxycarbonyl radical having from 2 to 6 carbon atoms; or
a phenyl, phenoxy, phenylthio, phenylsulfonyl or pyridyloxy radical, each of which can be optionally substituted by one or more of the following groups:
a halogen atom;
an alkyl, haloalkyl, cyanoalkyl, alkoxy, haloalkoxy, alkylthio, haloalkylthio or alkylsulfonyl radical having from 1 to 6 carbon atoms, the haloalkyl, haloalkoxy and haloalkylthio radicals bearing 1 or more halogen atoms as substituents;
a cycloalkyl, halocycloalkyl, alkenyl, alkynyl, alkenyloxy, alkynyloxy, alkenylthio or alkynylthio radical having from 3 to 6 carbon atoms, the halocycloalkyl radical bearing 1 or more halogen atoms as substituents;
a nitro, cyano or thiocyanato group;
an amino radical optionally mono- or disubstituted by an alkyl or acyl radical having from 1 to 6 carbon atoms or an alkoxycarbonyl radical having from 2 to 6 carbon atoms; or
a phenyl, phenoxy, phenylthio, phenylsulfonyl or pyridyloxy radical;

and the corresponding agriculturally acceptable salts.

Preferred compounds of this third major aspect of the invention have the formula:

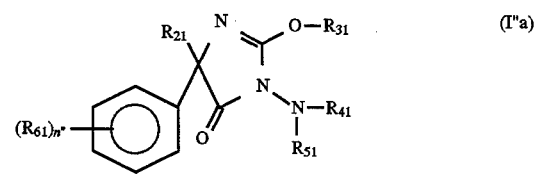

(I"a)

wherein $R_{21}$ to $R_{61}$ have the same meanings as above and n" is 0, 1, 2 or 3.

$R_{41}$ preferably represents phenyl, substituted phenyl, pyridyl or substituted pyridyl. $R_{51}$ preferably represents hydrogen or acyl (e.g. acetyl).

In a fourth major aspect of the present invention, it has been found that the objects of the invention noted hereinabove can be accomplished by means of fungicidal optically active 2-imidazolin-5-one and 2-imidazoline-5-thione derivatives. The corresponding racemic compounds are compounds of formulae (I), (I') and (II") hereinabove, which are described in earlier copending parent U.S. Ser. No. 07/993,700 fried Dec. 21, 1992, now abandoned (corresponding to European Patent Publication No. EP 0551048, published Jul. 14, 1993), in earlier copending parent U.S. Ser. No. 08/156,647, filed Nov. 24, 1993, now abandoned (corresponding to European Patent Publication No. EP 0599749, published Jun. 1, 1994), and in earlier copending parent International Application No. PCT/FR93/00647, filed Jun. 29, 1993 (published as International PCT Publication No. WO 94/01410, on Jan. 20, 1994); optically active isomers are described in earlier copending parent International Application No. PCT/FR93/00647 and most especially in earlier copending parent U.S. Ser. No. 08/262,459, filed Jun. 20, 1994, now abandoned.

In accord with the fourth major aspect of the present invention, it has been discovered that one of the optical isomers of the racemic compounds referred to above has a biological activity which is much greater than that of the other isomer and that of the racemic mixture.

A further object of the present invention is therefore to provide new optically active compounds which are useful in controlling fungal diseases of crops.

Another further object of the invention is to provide new 2-imidazolin-5-one and 2-imidazoline-5-thione derivatives which are active at a dose which is reduced with respect to that of the racemic derivatives.

It has been found that these objects can be achieved by virtue of the products of the invention which are optically active 2-imidazolin-5-one or 2-imidazoline-5-thione derivatives of general formula (I'''):

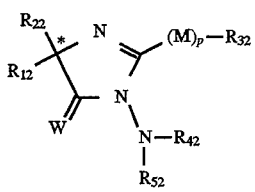 (I''')

wherein:

W represents an oxygen or sulfur atom or an S=O group;

M represents an oxygen or sulfur atom, or an optionally halogenated $CH_2$ radical;

p is an integer equal to 0 or 1;

\* means the asymmetric carbon atom corresponding to a stereospecific configuration;

$R_{12}$ and $R_{22}$ are different and represent:
- an alkyl or haloalkyl radical having 1 to 6 carbon atoms;
- an alkoxyalkyl, alkylthioalkyl, alkylsulfonylalkyl, monoalkylaminoalkyl, alkenyl or alkynyl radical having 2 to 6 carbon atoms;
- a dialkylaminoalkyl or cycloalkyl radical having 3 to 7 carbon atoms;
- an aryl radical comprising phenyl, naphthyl, thienyl, furyl, pyridyl, benzothienyl, benzofuryl, quinolyl, isoquinolyl or methylenedioxyphenyl, optionally substituted by 1 to 3 groups chosen from $R_{62}$; or
- an arylalkyl, aryloxyalkyl, arylthioalkyl or arylsulfonylalkyl radical, the terms aryl and alkyl having the definitions given above with respect to formula (I''');

or $R_{12}$ and $R_{22}$ can form, with the carbon to which they are bonded on the ring, a carbocycle or a heterocycle having from 5 to 7 atoms, it being possible for these rings to be fused to a phenyl, optionally substituted by 1 to 3 groups chosen from $R_{62}$;

$R_{32}$ represents:
- a hydrogen or an optionally halogenated $C_1$–$C_2$ alkyl radical, when p is equal to 0 or $(M)_p$ is a $CH_2$ radical; or
- an optionally halogenated $C_1$–$C_2$ alkyl radical, when $(M)_p$ represents an oxygen or sulfur atom;

$R_{42}$ represents:
- the hydrogen atom;
- an alkyl group having 1 to 6 carbon atoms;
- an alkoxyalkyl, alkylthioalkyl, haloalkyl, cyanoalkyl, thiocyanatoalkyl, alkenyl or alkynyl group having 2 to 6 carbon atoms;
- a dialkylaminoalkyl, alkoxycarbonylalkyl or N-alkylcarbamoylalkyl group having 3 to 6 carbon atoms;
- an N,N-dialkylcarbamoylalkyl group having 4 to 8 carbon atoms;
- an aryl radical, comprising phenyl, naphthyl, thienyl, furyl, pyridyl, pyrimidinyl, pyridazinyl, pyrazinyl, benzothienyl, benzofuryl, quinolyl, isoquinolyl or methylenedioxyphenyl, optionally substituted by 1 to 3 groups chosen from $R_{62}$; or
- an arylalkyl, aryloxyalkyl, arylthioalkyl or arylsulfonylalkyl radical, the terms aryl and alkyl having the definitions given above with respect to formula (I''');

$R_{52}$ represents:
- H, except when $R_{42}$ is H;
- an alkyl, haloalkyl, alkylsulfonyl or haloalkylsulfonyl radical having 1 to 6 carbon atoms;
- an alkoxyalkyl, alkylthioalkyl, acyl, alkenyl, alkynyl, haloacyl, alkoxycarbonyl, haloalkoxycarbonyl, alkoxyalkylsulfonyl or cyanoalkylsulfonyl radical having 2 to 6 carbon atoms;
- an alkoxyalkoxycarbonyl, alkylthioalkoxycarbonyl or cyanoalkoxycarbonyl radical having 3 to 6 carbon atoms;
- the formyl radical;
- a cycloalkyl, alkoxyacyl, alkylthioacyl, cyanoacyl, alkenylcarbonyl or alkynylcarbonyl radical having 3 to 6 carbon atoms;
- a cycloalkylcarbonyl radical having 4 to 8 carbon atoms;
- a phenyl; arylalkylcarbonyl, especially phenylacetyl or phenylpropionyl; arylcarbonyl, especially benzoyl, optionally substituted by 1 to 3 groups chosen from $R_{62}$ thienylcarbonyl; furylcarbonyl; pyridylcarbonyl; benzyloxycarbonyl; furfuryloxycarbonyl; tetrahydrofurfuryloxycarbonyl; thienylmethoxycarbonyl; pyridylmethoxycarbonyl; phenoxycarbonyl or (phenylthio)carbonyl, the phenyl being itself optionally substituted by 1 to 3 groups chosen from $R_{62}$; (alkylthio)carbonyl; (haloalkylthio)carbonyl; (alkoxyalkylthio)carbonyl; (cyanoalkylthio)carbonyl; (benzylthio)carbonyl; (furfurylthio)carbonyl; (tetrahydrofurfurylthio)carbonyl; (thienylmethylthio)carbonyl; (pyridylmethylthio)carbonyl or arylsulfonyl radical;
- a carbamoyl radical, optionally mono- or disubstituted by:
  - an alkyl or haloalkyl group having 1 to 6 carbon atoms;
  - a cycloalkyl, alkenyl or alkynyl group having 3 to 6 carbon atoms;
  - an alkoxyalkyl, alkylthioalkyl or cyanoalkyl group having 2 to 6 carbon atoms; or
  - a phenyl, optionally substituted by 1 to 3 $R_{62}$ groups;
- a sulfamoyl group, optionally mono- or disubstituted by:
  - an alkyl or haloalkyl group having 1 to 6 carbon atoms;
  - a cycloalkyl, alkenyl or alkynyl group having 3 to 6 carbon atoms;
  - an alkoxyalkyl, alkylthioalkyl or cyanoalkyl group having 2 to 6 carbon atoms; or
  - a phenyl, optionally substituted by 1 to 3 $R_{62}$ groups; or
- an alkylthioalkylsulfonyl group having 3 to 8 carbon atoms or a cycloalkylsulfonyl group having 3 to 7 carbon atoms;

or $R_{42}$ and $R_{52}$, taken together, can form, with the nitrogen atom to which they are attached, a pyrrolidino, piperidino, morpholino or piperazino group, optionally substituted by an alkyl having 1 to 3 carbon atoms;

$R_{62}$ represents:
- a halogen atom;
- an alkyl, haloalkyl, alkoxy, haloalkoxy, alkylthio, haloalkylthio or alkylsulfonyl radical having 1 to 6 carbon atoms;
- a cycloalkyl, halocycloalkyl, alkenyloxy, alkynyloxy, alkenylthio or alkynythio radical having 3 to 6 carbon atoms;
- the nitro or cyano group;
- an amino radical, optionally mono- or disubstituted by an alkyl or acyl radical having 1 to 6 carbon atoms or an alkoxycarbonyl radical having 2 to 6 carbon atoms; or
- a phenyl, phenoxy or pyridyloxy radical, these radicals optionally being substituted by 1 to 3 groups, which are identical or different, chosen from $R_{72}$; and $R_{72}$ represents:
- a halogen atom chosen from fluorine, chlorine, bromine or iodine;
- a linear or branched alkyl radical having from 1 to 6 carbon atoms;
- a linear or branched alkoxy or alkylthio radical having from 1 to 6 carbon atoms; or
- a linear or branched haloalkoxy or haloalkylthio radical having from 1 to 6 carbon atoms;
- a nitrile radical; or
- a nitro radical.

The invention also relates to the agriculturally acceptable salified forms of the compounds of formula (I'").

According to a preferred variant of the fourth major aspect of the invention, the optically active compounds according to the invention have the formula (I"'a):

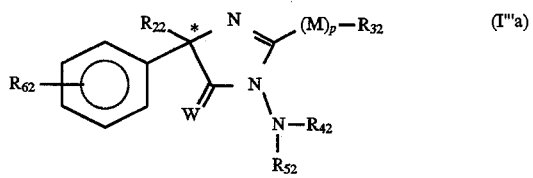

(I"'a)

in which the various symbols have the same meaning as in the formula (I'").

Finally, the compounds of the fourth major aspect of the invention will advantageously be chosen from the compounds of formula (I"'a) in which W represents an oxygen atom.

In accord with the present invention, it has been found that the configuration of the asymmetric carbon atom marked with an asterisk (*) in formula (I'"), i.e. in the 4-position of the ring, is very important to the fungicidal activity of the compounds of formula (I'") and that one of the two optical isomers, or enantiomers, has much greater fungicidal activity than the other member of the pair. It is therefore especially desirable to produce the enantiomer which has the greater fungicidal activity of the pair in optically pure form or to produce optically active compound in a form which is greatly enriched in the more fungicidally active enantiomer, for use in fungicidal compositions and for treating or preventing fungal disease. By "greatly enriched" form, it is meant that the optically active compound of formula (I'") contains no more than 20%, preferably no more than 5%, of the less fungicidally active of the pair of enantiomers. In other words, when the optically active compound of formula (I'") is in greatly enriched form, it should contain at least 80%, preferably at least 95%, of the more fungicidally active of the pair of enantiomers.

PROCESSES FOR THE PREPARATION OF COMPOUNDS OF FORMULA (I)

The compounds of formula (Ia) can be prepared according to the processes known per se described in the references (a) through (c) mentioned hereinabove in regard to formula (Ia) and in one of the following references:

(e) Biltz, H., *Chemische Berichte*, 42, 1792–1801 (1909);

(f) Chattelain, M. and Cabrier, P., *Bulletin de la Société Chimique de France*, 14 (1947), 639–642;

(g) Carrington, C. H. and Warring, W. S., *Journal of the Chemical Society*, (1950), 354–365;

(h) Lampert, K., Breuer, J. and Lemper-Streter, M., *Chemische Berichte*, 92, 235–239 (1959);

(i) Shalaby, A. and Daboun, H. A., *Journal für Praktische Chemie*, 313 (6), 1031–1038 (1971);

(j) Simig, G., Lemper, K. and Tamas, J., *Tetrahedron*, 29 (22), 3571–3578 (1973);

(k) Schmidt, U., Heimgartner, H. and Schmidt, H., *Helvetica Chemica Acta*, 62 (1979), 160–170; or (l) Muraoka, M., *Journal of the Chemical Society, Perkin Transactions I*, (1990), 3003–3007;

or according to one of the processes A, B, C or D described below.

The compounds of formula (Ib) can be obtained according to the process described by Böhme, Martin and Strahl in *Archiv der Pharmazie*, 313, 10–15 (1980) [reference (d) hereinabove] or according to one of the processes described below.

Process A: Process for the preparation of the compounds of formula (I).

The preparation of the compounds of formula (I) in which A is S by S-alkylation of the 2-thiohydantoins of formula (II) below is carried out according m the reaction scheme:

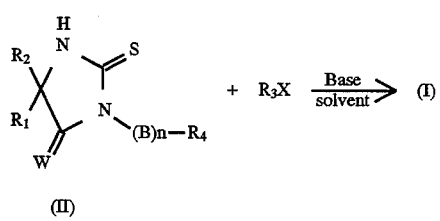

(II)

wherein $R_1$, $R_2$, $R_3$, $R_4$, B, W and n are as defined with formula (I) hereinabove and wherein X represents a chlorine, bromine or iodine atom or a sulfate group, or an alkylsulfonyloxy or arylsulfonyloxy group, alkyl and aryl being as defined above for $R_1$ and $R_2$. It is possible to use, as base, an alkoxide, for example potassium tert-butoxide, an alkali metal or alkaline-earth metal hydroxide, an alkali metal carbonate or a tertiary amine. It is possible to use, as solvent, ethers, cyclic ethers, alkyl esters, acetonitrile, alcohols having 1 to 3 carbon atoms, or aromatic solvents, for example tetrahydrofuran, at a temperature of between –5° C. and +80° C.

This process is suitable for the compounds in which W represents a sulfur or oxygen atom.

The 2-thiohydantoins of formula (II) above can be obtained according to processes described in the literature such as, for example, in the following references:

(e) Biltz, H., *Chemische Berichte*, 42, 1792–1801 (1909);

(n) Eberly and Dains, *Journal of the American Chemical Society*, 58, (1936), 2544–2547;

(o) Carrington, C. H., *Journal of the Chemical Society*, (1947), 681–686;

(g) Carrington, C. H. and Warring, W. S., *Journal of the Chemical Society*, (1950), 354–365;

(h) Lampert, K., Breuer, J. and Lemper-Streter, M., *Chemische Berichte*, 92, 235–239 (1959); or (i) Koltai, E., Nyitrai, J., Lempert, K. and Burics, L., *Chemische Berichte*, 104, 290–300 (1971);

or alternatively according to one of processes E or F described below and which form part of the invention.

Process B: Process for the preparation of the compounds of formula (Ic).

The preparation of the 2-methylthio-2-imidazolin-5-ones of formula (Ic) below by cyclization of the iminodithiocarbonates of formula (V) below is carried out according to the overall scheme:

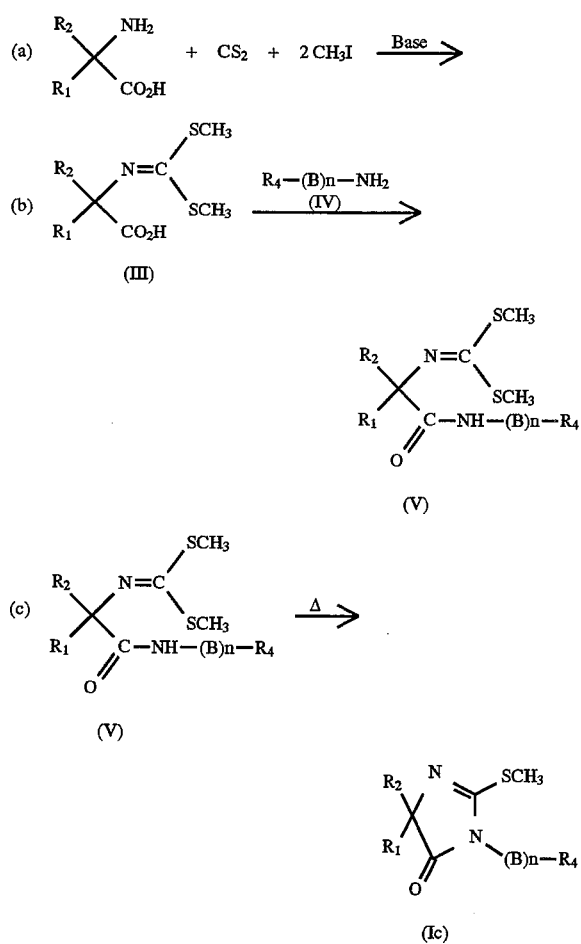

wherein $R_1$, $R_2$, $R_4$, B and n are defined as with formula (I) above.

Step (a):

The iminodithiocarbonates (III) can be prepared by carrying out the preparation according to the conditions described in the literature for analogous compounds, for example C. Alvarez Ibarra et al, *Tetrahedron Letters*, 26 (2), 243–246 (1985) or E. Mclendez et al, *Synthesis*, 1981, 961, according to the scheme:

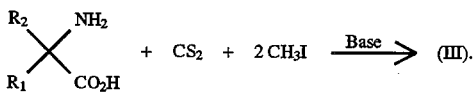

Step (b):

The compounds of formula (V) are obtained by condensing the compounds of formula (III) with mines or hydrazines of formula (IV). To carry out the condensation, the acid (III) must be activated in the acid chloride form, in the dicyclohexylisourea form using dicyclohexylcarbodiimlde or in the imidazolide form using carbonyldiimidazole. Condensation is carded out under the usual conditions for this type of reaction.

Step (c):

Cyclization of the compounds (V) is carried out by simple heating in an aromatic solvent at reflux. It is possible to use, as solvent, especially xylene, chlorobenzene or dichlorobenzene.

Process C: Derivatization of the compounds of formulae (Ibb) and (Idd).

Process C1: Process for the preparation of the compounds of formula (Ib) by N-derivatization of the compounds of formula (Ibb).

The compounds of formula (Ibb), that is, the compounds of formula (Ib) in which $R_5$ is a hydrogen atom, can be alkylated, acylated, alkoxycarbonylated, carbamoylated or sulfamoylated according to the following general scheme:

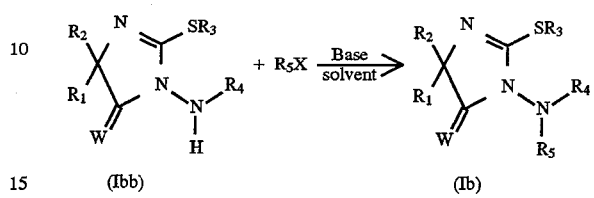

wherein $R_5$ is other than H, i.e. wherein $R_5$ represents an alkyl, alkoxycarbonyl acyl, arylcarbonyl, alkylsulfonyl, arylsulfonyl, carbamoyl or sulfamoyl group, such as defined above with respect to formula (I); X represents a halogen, a sulfate group or an optionally substituted phenoxy, or an alkylsulfonyloxy or arylsulfonyloxy group, or a group $R_5O$, when $R_5$ is acyl; and the other structural variables are defined as before with formula (I).

It is possible to use, as base, alkali metal hydrides, alkoxides or a tertiary amine. The reaction can be carried out at a temperature of between –30° C. and 50° C. It is possible to use as solvent, for example, ethers, cyclic ethers, dimethylformamide, dimethyl sulfoxide or aromatic solvents.

Carbamoylation of the compounds (Ibb) can be carried out by reacting them with isocyanates or isothiocyanates according to the scheme:

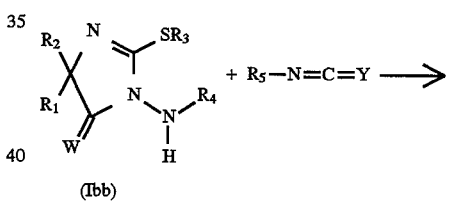

The reaction is carded out under the same conditions as those described above, it being possible for the base, however, to be used in catalytic quantity.

Process C2: Process for the preparation of the compounds of formula (Id).

The compounds of formula (Idd), that is, the compounds of formula (Id) in which $R_2$ is a hydrogen atom, can be alkylated in the 4-position according to the scheme:

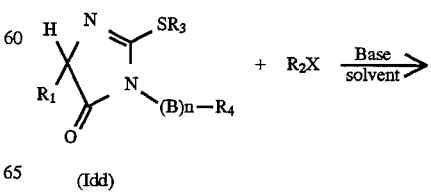

-continued

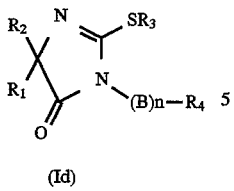

(Id)

wherein X represents a chlorine, bromine or iodine atom, and the other substiuents are defined as before except that $R_2$ is other than H, in an organic solvent in the presence of base. It is possible to use, as base, an alkoxide, a metal hydride or an amide. The reaction can be carried out at a temperature of between −30° C. and +80° C. It is possible to use, as solvent, ethers, cyclic ethers, dimethylformamide, dimethyl sulfoxide or aromatic solvents.

Process D: Process for the preparation of S-oxidized derivatives of the 2-imidazoline-5-thiones of formula (I).

The compounds of formula (1) in which W represents a S=O group are obtained by S-oxidizing the corresponding 2-imidazoline-5-thiones of formula (I) according to the scheme:

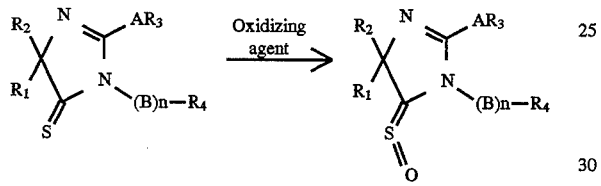

wherein $R_1$, $R_2$, $R_3$, $R_4$, A, B and n are defined as before. It is possible to use peroxides, especially peracids, as the oxidizing agent. The oxidizing agent must be used in a stoichiometric quantity. Oxidation is carried out in chloroform or in methylene chloride at a temperature of between −20° C. and +20° C.

Process E: Preparation of the dithiohydantoins of formula (VI) below.

The dithiohydantoins of formula (VI) below can be obtained by trapping the alpha anions of the isothiocyanates with isothiocyanates which cannot form anions according to the scheme:

$$R_1-CH-N=C=S \ + \ R_4-N=C=S \ \xrightarrow[\text{solvent}]{\text{Base}}$$
$\quad\ \ |$
$\quad R_2$

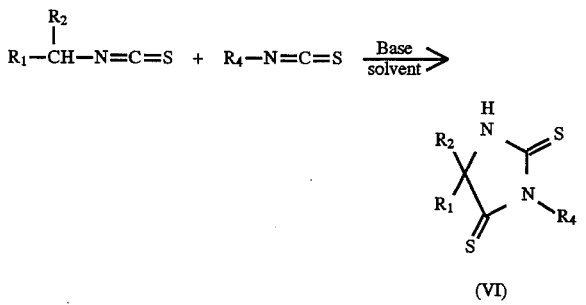

(VI)

wherein $R_1$, $R_2$ and $R_4$ are defined as with formula (I), provided that at least one of the groups $R_1$ or $R_2$ must be electron-withdrawing (aryl, substituted aryl, alkoxycarbonyl, or the like). The isothiocyanate $R_4$—NCS must not be able to form an anion; aryl isothiocyanates can be used in particular in this reaction. The reaction is carried out in the presence of base. It is possible to use, as base, potassium tert-butoxide, lithium or sodium bis (trimethylsilyl)amide or alkali metal hydrides. It is possible to use ethers or cyclic ethers as solvent. The reaction is carried out at a temperature below −60° C. The anion must be trapped as it is formed. To achieve this, the mixture of the two isothiocyanates is run onto the base in solution at a temperature below −60° C.

Process F: Preparation of the 2-thiohydantoins of formula (VII) below.

The preparation of the 2-thiohydantoins (VII) from the isothiocyanates derived from the amino acids (VIII) is carried out according to the reaction:

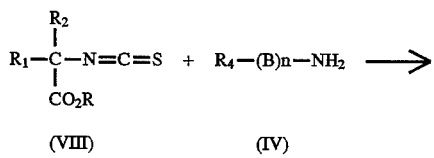

(VIII)                           (IV)

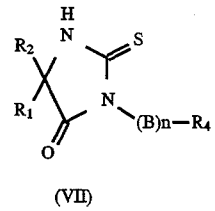

(VII)

wherein $R_1$, $R_2$, $R_4$, B and n have the same meanings as with formula (I).

Cyclization can be carried out in two ways:

thermally: in this case, the mixture of the reactants is heated at a temperature of between 110° C. and 180° C. in an aromatic solvent, such as toluene, xylene or the chlorobenzenes;

in basic medium: the cyclization is carried out in the presence of one equivalent of a base, such as an alkali metal alkoxide, an alkali metal hydroxide or a tertiary amine. Under these conditions, cyclization takes place at a temperature of between −10° C. and +80° C. It is possible to use ethers, cyclic ethers, alcohols, esters, DMF, DMSO and the like as solvent. The mixture is subsequently neutralized at room temperature.

The isothiocyanates can be prepared according to one of the processes mentioned in *Sulfur Reports*, 8 (5), 327–375 (1989).

Process G: Preparation of the compounds of formula (I) in a single stage.

During cyclization of the 2-thiohydantoins according to process F, if the cyclization is carried out in basic medium, the thiohydantoin is in the thiolate form at the end of the reaction and can be reacted directly with an alkyl halide (chloride, bromide or iodide) or alkyl sulfate $R_3X$ or with $R_3X$ in which X is an alkylsulfonyloxy or arylsulfonyloxy to form the corresponding compound of formula (I). Processes A and F are thus linked together according to the scheme:

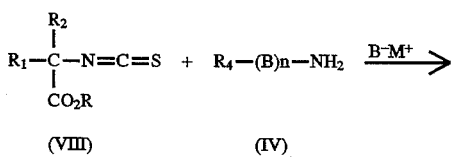

(VIII)                           (IV)

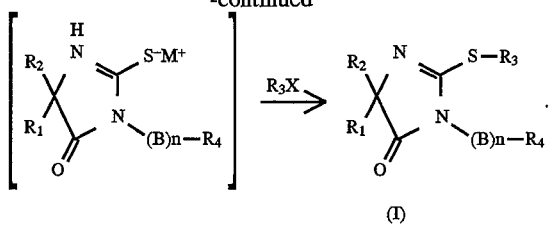

(I)

Process H: Preparation of the compounds of formula (Ie), that is the compounds of formula (I) in which (B)n is a sulfur atom.

These compounds can be obtained by reacting a sulfuryl chloride $R_4SCl$ with an imidazolinone of formula (IX) according to the scheme:

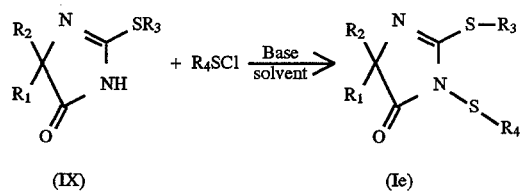

(IX)    (Ie)

wherein $R_1$, $R_2$, $R_3$ and $R_4$ are as defined with formula (I).

The reaction is carried out at a temperature of between $-20°$ C. and $+30°$ C., in the presence of one molar equivalent of a base. As base, it is possible to use alkali metal hydrides, alkali metal alkoxides or tertiary amines. As solvent, it is possible to use polar solvents, for example ethers, cyclic ethers, dimethylformamide, dimethyl sulfoxide or aromatic solvents. The imidazolinones of formula (IX) can be prepared by processes analogous to process A above.

PROCESSES FOR THE PREPARATION OF COMPOUNDS OF FORMULA (I')

PROCESS A:

Compounds of formula (I') in which n=0, that is, compounds having the formula (I'b):

(I'b)

wherein the structural variables are as defined with formula (I') hereinabove, can be prepared according to standard processes described in the literature:

(1) Cyclization of an α-amino acid amide of the formula:

(X)

with a carboxylic acid orthoester of the formula:

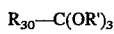

$R_{30}$—$C(OR')_3$ wherein R' represents a linear or branched alkyl radical having 1 to 4 carbon atoms, affords the corresponding compound of formula (I'b). This process has been described, for example, by J. Brunken and G. Bach in Chem. Ber., 89, 1363–1373 (1956) and S. Ginsburg in J. Org. Chem., 27, 4062–4064 (1962).

The amino acid amides of the formula (X) above can be prepared conventionally by reacting an amine of formula $R_{40}NH_2$ with an amino acid ester of formula (XI):

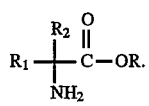

(XI)

The reaction can then be carried out according to the conditions described by J. Brunken and G. Bach in Chem. Ber., 89, 1363–1373 (1956).

(2) Reaction of an amine $R_{40}NH_2$ with an iminoester of the formula (XII):

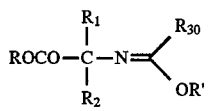

(XII)

affords the corresponding compound of formula (I'b). This process has been described in J. Chem. Soc., 1959, 1648 by G. Shaw et al.

The iminoesters (XII can be obtained by reaction of an amino acid ester (XI) with an imidate of the formula:

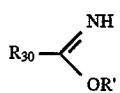

as described in Ber. dt. Chem. Ges., 47, 2545 (1914).

(3) The compounds of formula (I'c), that is, the compounds of formula (I'b) in which $R_{30}$ is a hydrogen atom, can be obtained by cyclization of an isonitrile derived from an amide of formula (XIII) in the presence of base, according to the scheme:

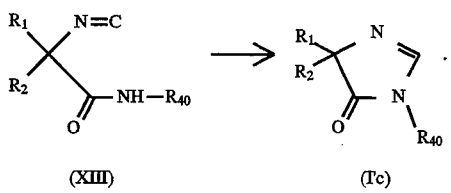

(XIII)    (I'c)

This process has been described by Belgian Patent Application No. 862,194 of 22 Dec. 1977.

(4) The compounds of formula (I'b) in which $R_2$ is other than hydrogen can be obtained by alkylation of the corresponding compounds of the formula (I'd), using a compound of the formula $R_2X$ as the alkylating agent, in basic medium according to the method described in the above-mentioned Belgian patent application, according to the scheme:

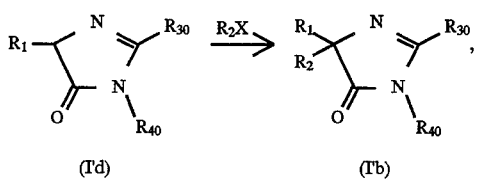

(I'd)    (I'b)

wherein $R_2$ is other than hydrogen.

(5) Reaction of an amine of the formula $R_{40}NH_2$ with an azalactone of the formula (XIV):

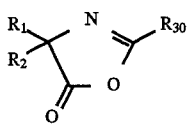 (XIV)

affords the corresponding compound of formula (I'b). This reaction can be carried out by acid catalysis (acetic acid, for example) or by basic catalysis. An example of the latter case can be found in the article by Ito et al, *Yakugaku Zasshi*, 1975, 95(1), 28–32.

PROCESS B:

The compounds of formula (I'a) can be obtained by analogy with one of the above-mentioned processes by reacting a hydrazine derivative of the formula $R_{40}NR_5NH_2$ in place of the amine derivative of the formula $R_{40}NH_2$. They can also be prepared according to a process which forms part of the invention, by hot cyclization of a hydrazide of the formula (XV):

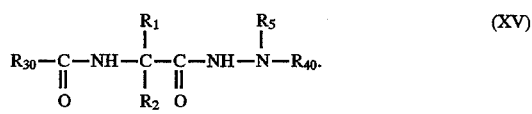 (XV)

The reaction is catalyzed by acids. Inorganic acids, alkylsulfonic acids, arylsulfonic acids, acidic resins or carboxylic acids can be used as the acid. The reaction can be carried out in aromatic solvents, halogenated hydrocarbons, ethers, cyclic ethers, ester or alcohols. It is carried out at a temperature between 50° C. and 150° C. The reaction is generally carried out at the reflux temperature of the solvent, the water being distilled off as it is formed.

The hydrazides of formula (XV) can be prepared according to one of the processes described in the literature, for example as enumerated below:

(1) Reaction of certain hydrazines of the formula $R_{40}NR_5NH_2$ with certain methyl, ethyl, propyl or butyl amino acid esters of the formula:

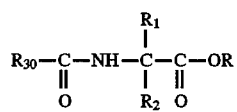

as described by German Patent Application 1,089,390 of 22 Sep. 1960 (*Chem. Ab.*, 1962, 56, 4860–4862), provides the corresponding hydrazides.

(2) Condensation of an N-acylated amino acid with a hydrazine in the presence of papain extracts in buffered aqueous solution according to the article by Niemann and Nichols in *J. Biol. Chem.*, 143, 1942, 191–201, affords the corresponding hydrazide.

(3) Reaction of a hydrazine $R_{40}NR_5NH_2$ with an azalactone of formula (XIV) hereinabove according to the reference by J. P. Branquet et al, *Bull. Soc. Chim. de France*, 1965, (10), 2942–2954, affords the corresponding hydrazides.

The azalactones of formula (XIV) are themselves described in the above-mentioned article.

(4) A preferred general access route analogous to process B(2) above consists in activating the acid in the imidazolide form (Reaction a) or the mixed anhydride form (Reaction b) in order to condense it with a hydrazine, as depicted below:

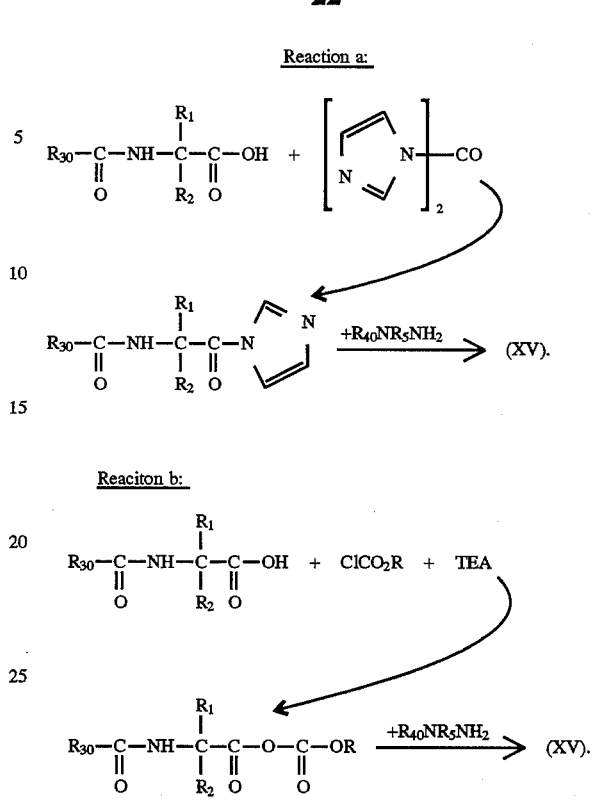

The condensation is carried out under the usual conditions for this type of reaction, as is illustrated in Examples 12 and 13 hereinbelow.

PROCESS C:

Another preferred route for preparing the compounds of formula (I'a) consists in reacting a hydrazine of the formula $R_{40}NR_5NH_2$ with an azalactone of the formula (XIV) hereinabove under certain conditions:

(1) By heating the reactants in an inert solvent in the presence of an acid in order to catalyze the reaction. Halogenated hydrocarbons, esters, aromatic solvents or alcohols can be used as the solvent. Inorganic acids, alkylsulfonic acids, arylsulfonic acids, acidic resins or carboxylic acids can be used to catalyze the reaction. The reaction is carried out at a temperature from 50° C. to 150° C.

This process is illustrated in Example 15 hereinbelow.

(2) By heating the mixture of the reactants in acetic acid at reflux in the presence of sodium acetate in order to catalyze the reaction.

These conditions are illustrated in Example 16 hereinbelow.

PROCESS D:

The compounds of formula (I'a) in which $R_5$ is other than a hydrogen atom are also possible starting from compounds of the formula (I'aa) below, which can be alkylated, acylated, alkoxycarbonylated, carbamoylated or sulfamoylated by $R_5X$ in the presence of base and solvent:

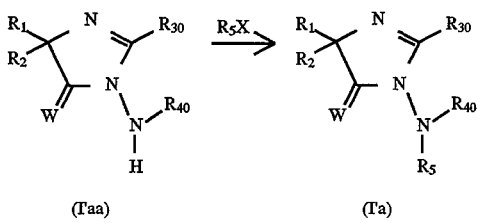

(I'aa) (I'a)

wherein $R_5$ here represents an alkyl, alkoxycarbonyl, acyl, arylcarbonyl, alkylsulfonyl, arylsulfonyl, carbamoyl or sulfamoyl group, as defined above, and X represents a halogen, a sulfate or optionally substituted phenoxy group, or an alkylsulfonyloxy or arylsulfonyloxy group, or a group $R_5O$, when $R_5$ is acyl.

Alkali metal hydrides, alkoxides or a tertiary amine can be used as base. The reaction can be carried out at a temperature between $-30°$ C. and $+50°$ C. Ethers, cyclic ethers, dimethylformamide, dimethyl sulfoxide or aromatic solvents, for example, can be used as solvent.

The carbamoylation or the thiocarbamoylation of the compounds of the formula (I'aa) can be carried out by reaction with isocyanates or isothiocyanates according to the scheme:

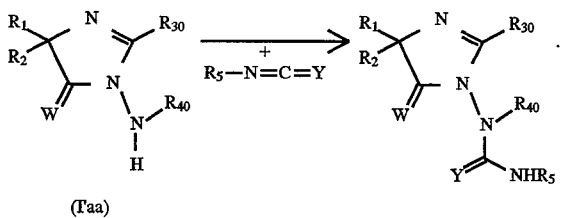

(I'aa)

The reaction is carried out under the same conditions as those described above, it being possible, however, for the base to be used in a catalytic amount.

PROCESS E:

The compounds of formula (I'ab) below, which are compounds of formula (I'a) in which the group $R_{30}$ is a hydrogen atom, can be obtained by reaction of dimethylformamide dimethyl acetal (DMFDMA) with an aminohydrazide of formula (XVI) according to the scheme:

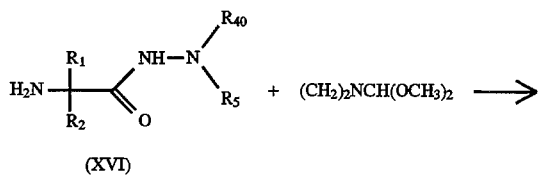

(XVI)

(I'ab)

The reaction is carried out at a temperature between $10°$ C. and $100°$ C. in DMFDMA used in excess.

The intermediate aminohydrazides of formula (XVI) can be obtained according to a new process by reacting the hydrochloride of the acid chloride of the corresponding α-amino acid in the presence of a base according to the scheme:

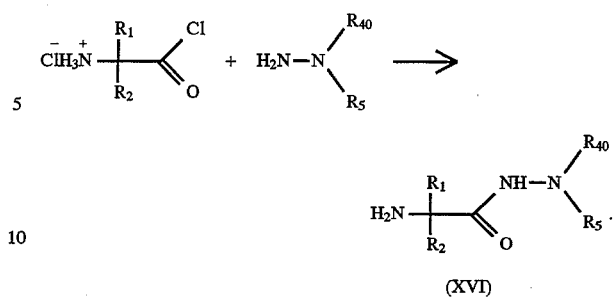

(XVI)

The reaction is carried out at a temperature between $-20°$ C. and $40°$ C. in cyclic or noncyclic ethers. Nitrogenous organic bases such as triethylamine or pyridine can be optionally used as the base. The intermediate acid chlorides can be obtained by the method described by S. Levine in *J. Am. Chem. Soc.*, 1953, Volume 76, 1392. They are then obtained by reacting phosphorus pentachloride with the α-amino acid according to the scheme below:

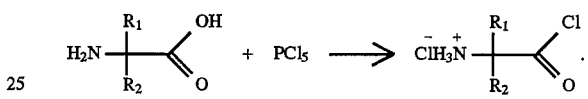

PROCESSES FOR THE PREPARATION OF COMPOUNDS OF FORMULA (I'')

The compounds of formula (I'') are obtained by reacting 2-alkylthio-2-imidazolin-5-ones of formula (XVII) with an alcohol $R_{31}OH$ in the presence of strong base, according to the scheme:

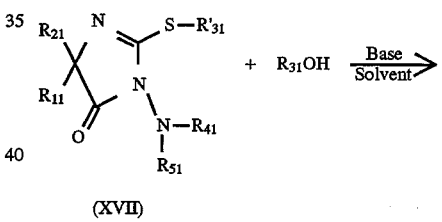

(XVII)

(I'')

wherein $R_{11}$, $R_{21}$, $R_{31}$ and $R_{41}$ have the same meaning as in formula (I'') hereinabove and $R'_{31}$ represents an alkyl group having from 1 to 3 carbon atoms.

As the strong base, an alkali metal alkoxide $R_{31}O^{-M+}$, an alkali metal hydroxide or a strong organic base can be used. The reaction is preferably carried out in the alcohol $R_{31}OH$ as solvent, using the corresponding sodium alkoxide $R_{31}O^-$ $Na^+$ as base. The reaction is carried out at a temperature of between about $20°$ C. and $80°$ C. The 2-alkylthio-2-imidazolin-5-ones of formula (XVII) are obtained according to one of the processes described hereinabove for the preparation of compounds of formula (I), in particular, for the preparation of compounds of formula (Ib) hereinabove. The acylation of the compounds of formula (I'') in which $R^{51}$ is a hydrogen atom, takes place according to classical methods.

Agriculturally acceptable salts of the compounds of formula (I″) may be prepared by known methods.

PROCESSES FOR THE PREPARATION OF COMPOUNDS OF FORMULA (I″)

The method of preparation of the compounds of formula (I″) is described in the following paragraph, according to two process variants A and B. The symbols represented in formula (I″) and its intermediates which appear in this description of the method of preparation retain the same meaning as in the general definition of the compounds of formula (I″) hereinabove, unless another definition is expressly attributed to them.

Variant A:

First Stage:

A first stage of this variant consists of the preparation of the optical isomers of formula (I″) from ex-amino acids which are optically pure or greatly enriched in one enantiomer. Optically active compound greatly enriched in a specific enantiomer is understood to mean a compound containing at least 80%, preferably 95%, of this enantiomer.

The optical isomers of formula (I″) are prepared according to three series of processes, depending on the meaning of the $(M)_p$-$R_{32}$ group.

Process (1): Preparation of the compounds of formula (I″) in which p=1 and M=S and W=O:

The compounds of formula (I″) in which p=1 and M=S and W=O are prepared by reaction of the compound of formula (XVIII):

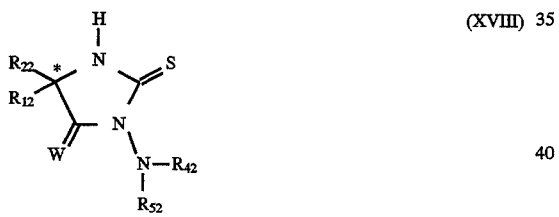

wherein W represents an oxygen atom, with the compound of formula $R_{32}X$, in which X represents the chlorine, bromine or iodine atom or the sulfate group or an alkylsulfonyloxy or arylsulfonyloxy group, alkyl and aryl being as defined above for $R_{12}$ and $R_{22}$. The reaction is carried out in a solvent and in the presence of a base. It is possible to use, as base, an alkoxide, for example potassium tert-butoxide, an alkali metal or alkaline-earth metal hydroxide, an alkali metal carbonate or a tertiary mine. It is possible to use, as solvent, ethers, cyclic ethers, alkyl esters, acetonitrile, alcohols containing 1 to 3 carbon atoms or aromatic solvents, for example tetrahydrofuran, at a temperature between –5 ° C. and +80 ° C.

A variant of the method described above consists in applying the so-called "one-pot" process depicted below, which is described hereinabove for the preparation of compounds of formula (I). This method consists in starting directly from the isothiocyanate of formula (XIX) which is treated with a compound of formula (XX) in a solvent and in the presence of a base as described above. The intermediate of formula (XVIIIa) in the salt form is not isolated but is treated directly with the compound of formula $R_{32}X$ in which X has the same meaning as in the preceding paragraph.

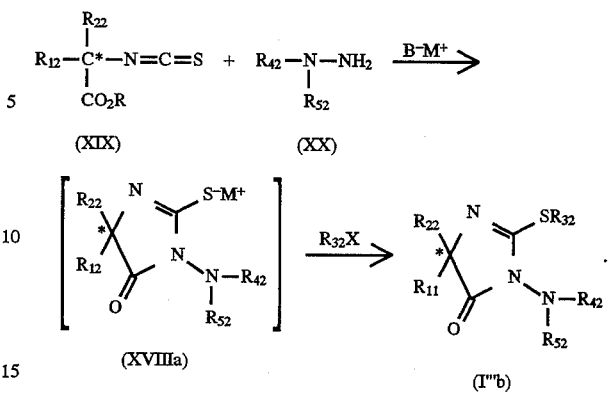

R is typically $C_1$–$C_6$ alkyl in formula (XIX) above.

The compound of formula (XVIII) in which W represents an oxygen atom can be prepared by a cyclization reaction between an isothiocyanate of formula (XIX):

wherein R represents $C_1$–$C_4$ alkyl, and a compound of formula (XX):

The cyclization reaction can be carried out in two ways:

(a) thermally: in this case, the mixture of the reactants is heated at a temperature between 110° C. and 180° C. in an aromatic solvent such as toluene, xylene or chlorobenzenes;

(b) in the basic medium: the cyclization reaction is carried out in the presence of one equivalent of base such as an alkali metal alkoxide, an alkali metal hydroxide or a tertiary amine. Under these conditions, cyclization takes place at a temperature between –10° C. and +80° C. It is possible to use, as solvent, especially ethers, cyclic ethers, alcohols, esters, DMF or DMSO.

The isothiocyanates of formula (XIX) can be prepared according to one of the processes mentioned in *Sulfur Reports*, Volume 8 (5), 327–375 (1989), from the α-amino acid of formula (XXI) via the amino ester of formula (XXII):

in a way well known to those skilled in the art.

The amino esters of structure (XXII) can be obtained in a known way by:

(a) diastereoselective amination of a prochiral compound followed by deprotection of the chiral moiety as described by R. S, Atkinson et al, *Tetrahedron*, 1992, 48, 7713–30;

(b) resolution of the corresponding racemate with a chiral compound as described by Y. Sugi and S. Mitsui, *Bull. Chem. Soc. Japan*, 1969, 42, 2984–89; or (c) esterification of a chiral amino acid as described by D. J. Cram et al, *J. Am. Chem. Soc.*, 1961, 83, 2183–89.

Process (2): Preparation of the optical isomers of formula (I''') in which p=1 and M=O and W=O:

The compounds of formula (I''') in which p=1 and M=O and W=O are prepared by reacting the corresponding compound of formula (I''') in which p=1 and M=S [according to a process described hereinabove for the preparation of compounds of formula (I)] with an alcohol of the formula $R_{32}OH$, in a solvent, in the presence of a strong base and at a temperature between 50° C. and 80° C. It is possible to use, as the strong base, an alkali metal alkoxide $R_{32}O^-$ $Met^+$, in which $Met^+$ represents an alkali metal or alkaline-earth metal, an alkali metal hydroxide or a strong organic base. The reaction is preferably carried out by selecting the alcohol $R_{32}OH$ as solvent and by using the corresponding sodium alkoxide $R_{32}O^-Na^+$ as base.

Process (3): Preparation of the optical isomers of formula (I''') in which p=0:

The compounds of formula (I''') in which p=0 and $R_{32}$ is a hydrogen atom are obtained from the corresponding compound of formula (XXIII):

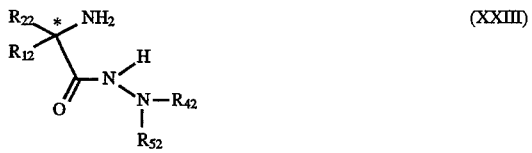

(XXIII)

by reacting the latter with dimethylformamide dimethyl acetal (DMFDMA). The reaction is carried out at a temperature between 10° C. and 1000° C., in excess DMFDMA.

The compound of formula (XXIII) is prepared from a compound of formula (XXIV):

(XXIV)

by reaction of the latter with the compound of formula (XX) above, at a temperature between −20° C. and 40° C., in a solvent consisting of a cyclic or non-cyclic ether, optionally in the presence of a base. The base is chosen from nitrogenous organic bases such as triethylamine or pyridine.

The compounds of formula (XXIV) can be obtained from the α-amino acid of formula (XXI) by observing the method described by S. Levine in *J. Am. Chem. Soc.*, 1953, Volume 76, 1392.

The optically active compounds of formula (I''') in which $R_{32}$ is an optionally halogenated $C_1-C_2$ alkyl radical and in which p=0 or p=1 and M=CH$_2$ are obtained from the compound of formula (XXV):

(XXV)

in which $R_{32}$ represents a $C_1-C_3$ alkyl radical, by reaction of the latter with the compound of formula (XX) above, under conditions deduced, by analogy, from the method set out in the article by J. P. Branquet et al in *Bull. Soc. Chim. de France*, 1965, (10), 2942–2954.

The same article gives a procedure at the end of which the compound of formula (XXV) can be prepared from the α-amino acid of formula (XXI).

Second Stage:

The method of access to the optically pure or greatly enriched α-amino acids of formula (XXI) used in the above stage is specified in this second stage of Variant A.

These α-amino acids can be obtained according to one of the following methods:

(1) by diastereoselective synthesis and then suppression of the chiral moiety, as described by M. Chaari, A. Jenhi, J. P. Lavergne and P. Viallefont in *Tetrahedron*, 1991, 4, 4619–4630, (2) by enzymatic resolution of the racemic amide, for which method the following references may usefully be consulted:

R. M. Kellog, E. M. Meijer et al, *J. Org. Chem.*, 1988, 53, 1826–1828; and

D. Rossi and A. Calcagni, *Experimentia*, 1985, 41, 35–37;

(3) by hydrolysis of a chiral amino acid precursor such as, for example:

(a) a formyl amino acid of structure (XXVI) below, as described by MacKenzie and Clough, *J. Chem. Soc.*, 1912, 390–397, or by D. J. Cram et al, *J. Am. Chem. Soc.*, 1961, 83, 2183–89; or (b) a hydantoin of structure (XXVII) as described in published British Patent Application No. 1,201,168:

(XXVI)

(XXVII)

The compounds of formulae (XXVI) and (XXVII) can be obtained by resolution of the corresponding racemic modification with a chiral compound as described by MacKenzie and Clough, *J. Chem. Soc.*, 1912, 390–397, or by D. J. Cram et al, *J. Am. Chem. Soc.*, 1961, 83, 2183–89, for the compound (XXVI); or as described in published International Patent Application No. 92/08702 for the compound (XXVII).

Variant B:

According to a second variant of the process for the preparation of the optical isomers of formula (I'''), the latter are obtained from the corresponding racemic compounds by high performance liquid chromatography on a chiral stationary phase. A chiral stationary phase of Pirkle type with D-phenylglycine grafts is preferred.

The racemic compounds corresponding to the formula (I''') are prepared according to the methods described hereinabove for the preparation of the compounds of formulas (I), (I'), and (I''), which are the methods described and exemplified in parent U.S. Ser. No. 07/993,700, filed Dec. 21, 1992, now abandoned, parent U.S. Ser. No. 08/156,647, filed Nov. 24, 1993, now abandoned, and parent International Application No. PCT/FR93/00647, filed Jun. 29, 1993.

Another subject of the present invention is new optically active compounds useful especially as intermediates in the preparation of the compounds of formula (I'''). These intermediates have the formulae (XVIII), (XIX), (XXI), (XXIII), (XXIV) and (XXII):

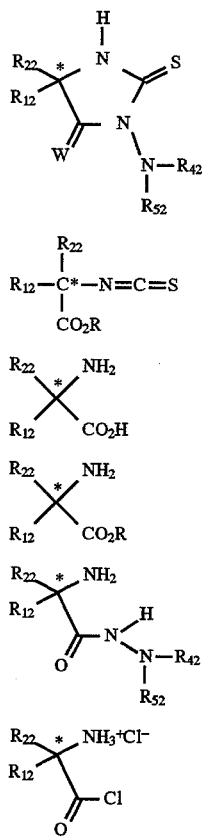 (XVIII)

(XIX)

(XXI)

(XXII)

(XXIII)

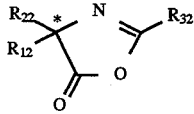 (XXIV)

wherein $R_{12}$, $R_{22}$, $R_{42}$ and $R_{52}$ have the same meanings as in the general formula (I''') of the invention;

and the formula (XXV):

(XXV)

wherein $R_{12}$ and $R_{22}$ have the same meaning as above and $R_{32}$ represents an optionally halogenated $C_1$–$C_3$ alkyl radical;

and the formula (XXVIIb):

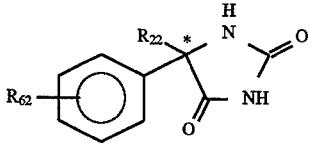 (XXVIIb)

wherein $R_{22}$ has the same meaning as above and $R_{62}$ represents a phenyl, phenoxy or pyridyloxy radical, these radicals optionally being substituted by 1 to 3 groups, which are identical or different, chosen from $R_{72}$ as defined above.

The EXAMPLES below are given by way of illustration only of the compounds according to the invention, of the processes for their preparation and of their antifungal properties.

The structures of all the products were established by at least one of the following spectral techniques: proton NMR spectrometry, carbon-13 NMR spectrometry, infrared spectrometry and mass spectrometry.

EXAMPLES OF THE PREPARATION OF COMPOUNDS OF FORMULA (I) AND INTERMEDIATES THERETO

In the tables below, the methyl and phenyl radicals are represented respectively by Me and Ph, and Cst means a physical constant, that is to say, either a melting point (M.p.) or the refractive index ($n_D^{20}$).

Example 1

Preparation of Compound 34 according to Process A.

0.9 g (3 mmol) of 3-benzyl-5-methyl-5-phenyl-2-thiohydantoin is dissolved in 30 ml of anhydrous tetrahydrofuran. The mixture is cooled to 0° C. and then 0.34 g (3 mmol) of potassium tert-butoxide is added. The mixture is left to react for 10 minutes at 0° C. and then 0.46 g (3.3 mmol) of methyl iodide is run in dropwise at this temperature: potassium iodide is observed to precipitate. The temperature of the mixture is allowed to return to room temperature. The mixture is diluted with 100 ml of ethyl acetate. The solution is washed 2 times with 100 ml of water on each occasion. The solution is dried over sodium sulfate and is then treated with active charcoal. The solution is concentrated under reduced pressure: 0.6 g of 1-benzyl-4-methyl-2-methylthio-4-phenyl-2-imidazolin-5-one (Compound 34) is recovered in the form of a pale-yellow solid melting at 68° C.

The compounds described below were prepared in the same way:

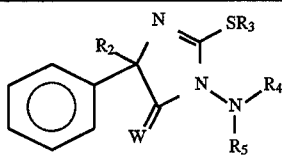

| No. | $R_2$ | $R_3$ | $R_4$ | $R_5$ | W | Cst |
|---|---|---|---|---|---|---|
| 1 | Me | Me | Ph | H | S | M.p. = 127° C. |
| 3 | Me | 2-oxopropyl | Ph | H | S | M.p. = 130° C. |
| 9 | Me | Me | Ph | H | O | M.p. = 149° C. |
| 10 | Me | Me | meta-tolyl | H | O | M.p. = 124° C. |
| 11 | Me | Me | para-tolyl | H | O | M.p. = 150° C. |
| 12 | Me | Et | Ph | H | O | M.p. = 118° C. |
| 13 | Me | Me | 4-fluroPh | H | O | M.p. = 144° C. |
| 14 | Me | allyl | Ph | H | O | M.p. = 92° C. |
| 15 | Me | Me | ortho-tolyl | H | O | M.p. = 92° C. |
| 16 | Me | Me | 3-chloroPh | H | O | M.p. = 120° C. |
| 17 | Me | isopropyl | Ph | H | O | M.p. = 95° C. |
| 18 | Me | Me | 4-chloroPh | H | O | M.p. = 149° C. |
| 19 | Me | Me | tert-butyl | H | O | M.p. = 73° C. |
| 20 | Me | Me | 2-chloroPh | H | O | M.p. = 134° C. |
| 22 | Me | Me | Ph | Me | O | M.p. = 124° C. |
| 23 | Me | Me | Ph | acetyl | O | M.p. = 132° C. |
| 24 | Me | Me | 4-methoxyPh | H | O | M.p. = 138° C. |
| 25 | Me | n-propyl | Ph | H | O | M.p. = 90° C. |
| 40 | Me | Me | 2-methoxyPh | H | O | M.p. = 110° C. |
| 41 | Me | Me | acetyl | H | O | M.p. = 55° C. |
| 43 | Me | Me | 4-$NO_2$—Ph | H | O | M.p. = 133° C. |
| 44 | Me | Me | 2-pyridyl | H | S | M.p. = 114° C. |
| 45 | Me | Me | 2-pyridyl | H | O | M.p. = 147° C. |
| 46 | Me | Me | 3-pyridyl | H | O | M.p. = 140° C. |
| 47 | Me | Me | 3-pyridyl | H | S | M.p. = 176° C. |
| 54 | Me | Me | 2,6-$Me_2$Ph | H | S | M.p. = 146° C. |
| 73 | Me | Me | 2-thiazolyl | Me | O | M.p. = 116° C. |
| 75 | Me | $CHF_2$ | Ph | H | O | M.p. = 80° C. |
| 80 | Me | Me | 3-pyridyl-CH= | — | O | M.p. = 92° C. |
| 81 | Me | Me | 2-pyridyl-CH= | — | O | M.p. = 106° C. |
| 82 | Me | Me | 4-Me—$SO_2$—PH | H | O | M.p. = 130° C. |

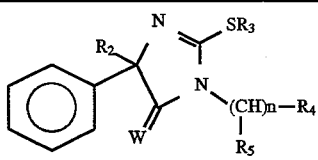

| No. | $R_2$ | $R_3$ | $R_4$ | n | $R_5$ | W | Cst |
|---|---|---|---|---|---|---|---|
| 26 | Me | Me | Ph | 0 | — | S | M.p. = 123° C. |
| 27 | Ph | Me | Ph | 0 | — | S | M.p. = 120° C. |
| 28 | Me | Me | Me | 0 | — | S | M.p. = 85° C. |
| 29 | Ph | Me | Me | 0 | — | S | M.p. = 144° C. |
| 30 | Me | Me | Ph | 0 | — | O | M.p. = 70° C. |
| 31 | Me | Me | Me | 0 | — | O | M.p. = 58° C. |
| 32 | Ph | Me | Me | 0 | — | O | M.p. = 170° C. |
| 33 | H | Me | Ph | 0 | — | O | M.p. = 250° C. |
| 34 | Me | Me | Ph | 1 | H | O | M.p. = 68° C. |
| 35 | Me | Me | 2-thienyl | 1 | H | O | M.p. = 76° C. |
| 36 | Me | Me | Me | 1 | Me | O | $n_D^{20}$ = 1.553 |
| 37 | Me | Me | 2-furyl | 1 | H | O | "honey-like consistency" |
| 38 | Me | Me | 3-pyridyl | 0 | — | O | "honey-like consistency" |
| 50 | Ph | Me | Me | 0 | H | S | M.p. = 144° C. |
| 52 | Me | Me | Ph | 1 | $CO_2Me$ | O | "honey-like consistency" |
| 57 | Me | Me | 2-MePh | 0 | — | O | "honey-like consistency" |

The following were also prepared:

4-(3-pyridyl)-4-methyl-1-(N-phenylamino)-2-methylthio-2-imidazolin-5-one (Compound 51: M.p. 156° C.);

4-phenyl-4-methyl-1-(benzyloxy)-2-methylthio-2-imidazolin-5-one (Compound 56: honey-like consistency).

Example 2

Preparation of Compound 7 according to Process B.

(a) N-[bis(methylthio)methylene]-2-phenylglycine [compound (III) in which $R_1$=phenyl and $R_2$=H]:

100 g (0.66 mol) of phenylglycine are dissolved at +5° C. in 335 g of 22% aqueous potassium hydroxide (1.3 mol). 55.3 g of carbon disulfide are added while stirring the mixture vigorously: a precipitate appears and the mixture rams orange in color. The mixture is left to react for 3 hours at room temperature and then 103 g (0.73 mol) of methyl iodide are run in while keeping the temperature of the mixture below 30° C. The mixture is left to react for 0.5 hour and then 74 g (0.66 mol) of a 50% potassium hydroxide solution are added. The mixture is left to react for 0.5 hour and then 103 g of methyl iodide are again run in and left to react for 1 hour. The mixture is diluted with 300 ml of water. The mixture is acidified to pH=4 with 1N hydrochloric acid. The product is extracted with 500 ml of ethyl acetate. The solution is dried over magnesium sulfate and then concentrated under reduced pressure. 49.5 g of N-[bis(methylthio)methylene]-2-phenylglycine (yield=31%) are recovered in the form of a yellow solid melting at 112° C.

(b) 2'-(metachlorophenyl)[N-(bis(methylthio)methylene)-2-phenylglycyl]hydrazide (compound V with $R_1$=phenyl, $R_2$=H, $R_4$=metachlorophenyl, n=1, B=NH):

3.38 g (16.4 mmol) of dicyclohexylcarbodiimide are added to a solution of 2.95 g (16.4 mmol) of N-[bis(methylthio)methylene]-2-phenylglycine in methylene chloride (40 ml), and the mixture is then left to react for 0.5 hour at room temperature. 2.34 g (16.4 mmol) of metachlorophenylhydrazine are added. The mixture is heated for 0.5 hour at 30° C. The insoluble material is filtered off. The filtrate is washed with 2 times 30 ml of water on each occasion. The solution is concentrated: a honey-like product is obtained which is purified by chromatography on a silica column. After purification, 2.5 g of 2'-(metachlorophenyl)[N-(bis(methylthio)methylene)-2-phenylglycyl]hydrazide are recovered in the form of a pinkish powder melting at 146° C.

(c) 1-Metachlorophenylamino-2-methylthio4-phenyl-2-imidazolin-5-one (compound 7):

1.92 g (5 mmol) of 2'-(metachlorophenyl)[N-(bis(methylthio)methylene)-2-phenylglycyl]hydrazide is dissolved in 30 ml of xylene. The reaction mixture is heated for 4 hours at reflux. The mixture is concentrated under reduced pressure. The resulting honey-like product is triturated with 10 ml of ether: the product crystallizes. The precipitate is filtered and the product is dried in a desiccator under vacuum. Compound 7 is thus obtained, with a yield of 56%, in the form of a yellow powder melting at 196° C.

By carrying out the preparation in a similar way, the compounds which appear in the following table were prepared:

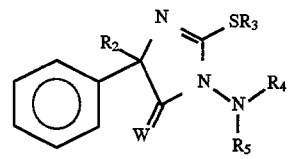

| No. | $R_2$ | $R_3$ | $R_4$ | $R_5$ | W | Cst |
|---|---|---|---|---|---|---|
| 4 | H | Me | 2-chloroPh | H | O | M.p. = 130° C. |
| 5 | H | Me | Ph | H | O | M.p. = 190° C. |
| 6 | H | Me | 4-chloroPh | H | O | M.p. = 162° C. |
| 7 | H | Me | 3-chloroPh | H | O | M.p. = 196° C. |
| 8 | H | Me | meta-tolyl | H | O | M.p. = 182° C. |
| 59 | H | Me | 2,4-$(CH_3)_2$Ph | H | O | M.p. = 64° C. |
| 61 | H | Me | 2,5-$(CH_3)_2$Ph | H | O | M.p. = 162° C. |
| 63 | H | Me | 2-EtPh | H | O | M.p. = 126° C. |
| 69 | H | Me | 2,5-$(Cl)_2$Ph | H | O | M.p. = 144° C. |
| 71 | H | Me | 3,5-$(Cl)_2$Ph | H | O | M.p. = 146° C. |

4-Phenyl-1-(N-phenylamino)-2-methylthio-2-imidazolin-5-one (Compound 120) was also prepared.

Example 3

Preparation of 4-methyl-1-(N-methyl-N-phenylamino)-2-methylthio-4-phenyl-2-imidazolin-5-one (Compound 22) by alkylation (methylation) according to Process C1:

0.4 g (3.5 mmol) of potassium tert-butoxide is added to a solution of 4-methyl-1-phenylamino-2-methylthio-4-phenyl-2-imidazolin-5-one (Compound 9) (1 g, 3.2 mmol) in anhydrous tetrahydrofuran (30 ml), cooled beforehand to 0° C. The mixture is left to react for 0.5 hour at 0° C. 0.5 g (3.5 mmol) of methyl iodide is then added and then the mixture is left to react for 0.5 hour at room temperature. The reaction mixture is poured into 100 ml of water and the product is extracted with 100 ml of diethyl ether. The ethereal solution is dried over magnesium sulfate and then concentrated. The product crystallizes when triturated in 10 ml of diisopropyl ether. It is filtered and then dried under vacuum. 0.73 g (yield: 70%) of Compound 22 is thus obtained in the form of a pale-yellow powder melting at 124° C.

Example 4

Preparation of 4-methyl-1-(N-acetyl-N-phenylamino)-2-methylthio-4-phenyl-2-imidazolin-5-one (Compound 23) by acylation (acetylation) according to Process C1:

0.4 g (3.5 mmol) of potassium tert-butoxide is added to a solution of 4-methyl-1-phenylamino-2-methylthio-4-phenyl-2-imidazolin-5-one (Compound 9) (1 g, 3.2 mmol) in anhydrous tetrahydrofuran (30 ml), cooled beforehand to 0° C. The mixture is left to react for 0.5 hour at 0° C. 0.25 g (3.5 mmol) of acetyl chloride is then added and the mixture is left to react for 0.5 hour at room temperature. The reaction mixture is poured into 100 ml of water and the product is extracted with 100 ml of diethyl ether. The ethereal solution is washed with water to neutrality. The solution is dried over magnesium sulfate and then concentrated. A honey-like product is obtained which is purified by chromatography on a silica column. The purified product crystallizes from diisopropyl ether. 0.25 g of Compound 23 is obtained in the form of a white powder melting at 132° C.

By carrying out the preparation in the same way, Compounds 39 and 42 were obtained.

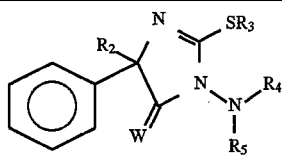

| No. | R₂ | R₃ | R₄ | R₅ | W | Cst |
|---|---|---|---|---|---|---|
| 23 | Me | Me | Ph | acetyl | O | M.p. = 132° C. |
| 39 | Me | Me | Ph | formyl | O | "honey-like consistency" |
| 42 | Me | Me | Ph | tBuOCO | O | "honey-like consistency" |

Example 5

Preparation of 4-ethyl-2-methylthio-4-phenyl-1-phenylamino-2-imidazolin-5-one (Compound 48) according to Process C2:

0.55 g of potassium tert-butoxide is added to a solution of 1.5 g (5.05 mmol) of 2-methylthio-4-phenyl-1-phenylamino-2-imidazolin-5-one (Compound 5) in 50 ml of anhydrous tetrahydrofuran. The mixture is left to react for 30 minutes at room temperature and then 0.8 g (5.05 mmol) of ethyl iodide is added. The mixture is left to react for 1 hour at room temperature. The mixture is diluted with 150 ml of ethyl acetate. The solution is washed with water and then concentrated under reduced pressure. The product is purified by chromatography on a silica column (Merck 60H silica; eluent: 25% ethyl acetate/75% heptane). 0.65 g of Compound 48 is obtained in the form of a beige powder melting at 147° C.

By carrying out the preparation in the same way, Compound 49 was obtained. The other compounds listed below can also be obtained in this manner.

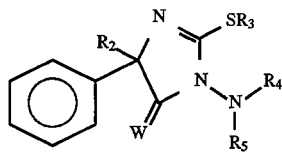

| No. | R₂ | R₃ | R₄ | R₅ | W | Cst |
|---|---|---|---|---|---|---|
| 48 | Et | Me | Ph | H | O | M.p. = 147° C. |
| 49 | iso-Pr | Me | Ph | H | O | M.p. = 135° C. |
| 60 | Me | Me | 2,4-(Me)₂Ph | H | O | "honey-like consistency" |
| 62 | Me | Me | 2,5-(Me)₂Ph | H | O | M.p. = 160° C. |
| 64 | Me | Me | 2-EtPh | H | O | "honey-like consistency" |
| 65 | Me | Me | 2,4-(Cl)₂Ph | H | O | |
| 66 | Me | Me | 1-naphthyl | H | O | M.p. = 174° C. |
| 70 | Me | Me | 2,5-(Cl)₂Ph | H | O | M.p. = 180° C. |
| 72 | Me | Me | 3,5-(Cl)₂Ph | H | O | M.p. = 200° C. |
| 74 | CHF₂ | Me | Ph | H | O | M.p. = 124° C. |
| 79 | Me | Me | 2-CF₃—Ph | H | O | M.p. = 91° C. |

4-Methyl-2-methylthio-4-(4-fluorophenyl)-1-phenylamino-2-imidazolin-5-one (Compound 68) was also prepared.

Example 6

Preparation of Compound 2 according to Process D:

1.7 g (5.2 mmol) of 4-methyl-2-methylthio-4-phenyl-1-phenylamino-2-imidazoline-5-thione (compound 1) is dissolved in 20 ml of chloroform. The solution is cooled to −10° C. and then a solution of 1.35 g (5.5 mmol) of metachloroperbenzoic acid and 30 ml of chloroform is added over 10 minutes. On completion of addition, the temperature is allowed to return to room temperature. The mixture is washed with a saturated aqueous sodium bicarbonate solution and then with distilled water. The organic phase is treated with active charcoal and then concentrated. The resulting honey-like product is taken up in 20 ml of ether: the product dissolves and then a beige solid precipitates. The precipitate is filtered. The product is dried under reduced pressure. 0.4 g (yield: 25%) of Compound 2 is thus obtained in the form of a beige powder melting at 150° C.

| No. | R₂ | R₃ | R₄ | R₅ | W | Cst |
|---|---|---|---|---|---|---|
| 2 | Me | Me | Ph | H | S=O | M.p. = 150° C. |

Example 7

Preparation of 3,5-diphenyl-5-methyldithiohydantoin according to Process E:

15.1 g (122 mmol) of potassium tert-butoxide are dissolved in 200 ml of tetrahydrofuran in a 500 ml, three-necked, round-bottomed flask under a dry argon atmosphere. The solution is cooled to −70° C. A solution containing 20 g (122 mmol) of alpha-methylbenzyl isothiocyanate, 16.55 g (122 mmol) of phenyl isothiocyanate and 50 ml of tetrahydrofuran is run in dropwise while keeping the temperature of the mixture below −60° C. On completion of addition, the mixture is held for 0.5 hour at −70° C. and then is left to return to room temperature. The mixture is poured into 500 ml of water. The mixture is acidified to pH=1 by addition of N hydrochloric acid. The product is extracted with ethyl acetate (2 extractions, each with 150 ml of solvent). The solution is dried over magnesium sulfate. The solution is concentrated under reduced pressure. The product is crystallized from 50 ml of ether. The precipitate is filtered. 21 g (yield: 58%) of 3,5-diphenyl-5-methyldithiohydantoin are thus obtained as a yellow powder melting at 157° C.

Example 8

Preparation of 3,5-diphenyl-5-methyl-2-thiohydantoin according to Process F:

4.7 g (20 mmol) of ethyl 2-isothiocyanato-2-phenylpropionate are dissolved in 40 ml of xylene. 2.16 g (20 mmol) of phenylhydrazine are added and the mixture is heated for 4 hours at reflux. The mixture is cooled to room temperature and a beige solid precipitates. The precipitate is filtered, washed with 5 ml of diisopropyl ether and then dried under vacuum. 4.6 g (yield=77%) of 3,5-diphenyl-5-methyl-2-thiohydantoin are thus obtained in the form of a beige powder melting at 164° C.

Example 9

Preparation of 5-methyl-5-phenyl-3-(2-pyridylamino)-2-thiohydantoin according to Process F:

2 g (9 mmol) of methyl 2-isothiocyanato-2-phenylpropionate are dissolved in 30 ml of tetrahydrofuran. A solution containing 0.99 g of 2-hydrazinopyridine and 10 ml of tetrahydrofuran is added: the temperature of the mixture rises from 20° to 30° C. and a solid precipitates. The mixture is allowed to react for 0.5 hour at 30° C. and then is cooled to 5° C. A solution containing 1 g of potassium tert-butoxide and 10 ml of tetrahydrofuran is then added: the mixture becomes violet in color. The mixture is left to return to room temperature and is left to react for 2 hours. The mixture is poured into 150 ml of water. The mixture is neutralized with acetic acid. The product is extracted with 150 ml of ethyl acetate. The solution is washed with water, dried over magnesium sulfate and then treated with active charcoal. The solution is concentrated and the product is crystallized from 20 ml of diethyl ether. The above-mentioned product is filtered and is dried under vacuum. 1.6 g (yield: 60%) of 5-methyl-5-phenyl-3-(2-pyridylamino)-2-thiohydantoin is obtained as a pale-yellow solid melting at 80° C.

The compounds of formula (VII) collated in the following table, which are intermediates of the compounds of formula (I) and are numbered from number 1001, were prepared according to this process:

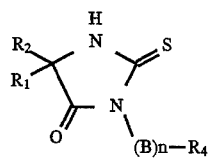

(VII)

wherein $R_1$=methyl and $R_2$=phenyl:

| No. | n | B | $R_4$ | Yield | M.p. |
|---|---|---|---|---|---|
| 1001 | 1 | NH | Ph | 66% | 164° C. |
| 1002 | 1 | NH | meta-tolyl | 62% | 174° C. |
| 1003 | 1 | $CH_2$ | Ph | 46% | 125° C. |
| 1004 | 1 | NH | para-tolyl | 13% | 162° C. |
| 1005 | 1 | $CH_2$ | 2-thienyl | 49.5% | 134° C. |
| 1006 | 1 | NH | 4-fluoroPh | 30% | 162° C. |
| 1007 | 1 | NH | ortho-tolyl | 38% | 162° C. |
| 1008 | 0 | — | isopropyl | 60.5% | 146° C. |
| 1009 | 1 | NH | 3-chloroPh | 32% | 78° C. |
| 1010 | 1 | NH | tert-butyl | 18% | 120° C. |
| 1011 | 1 | NH | 4-chloroPh | 24% | 196° C. |
| 1012 | 1 | NH | 2-chloroPh | 69% | 172° C. |
| 1013 | 0 | — | piperidino | 32% | 206° C. |
| 1014 | 1 | NH | 4-methoxyPh | 27% | 146° C. |
| 1015 | 1 | NH | 2-methoxyPh | 29% | 214° C. |
| 1016 | 1 | $CH_2$ | 2-furyl | 39% | 105° C. |
| 1017 | 1 | NH | acetyl | 42% | 200° C. |
| 1018 | 1 | NH | 4-$NO_2$-Ph | 41% | 234° C. |
| 1019 | 1 | NH | 2-pyridyl | 60% | 80° C. |
| 1020 | 1 | NH | 3-pyridyl | 17% |  |

Example 10

Preparation of Compound 9 according to Process G:

11.1 g (50 mmol) of methyl 2-isothiocyanato-2-phenylpropionate are dissolved in 150 ml of anhydrous tetrahydrofuran. A solution containing 5.4 g (50 mmol) of phenylhydrazine and 50 ml of anhydrous tetrahydrofuran is added progressively over 10 minutes: the temperature of the mixture rises to 35° C. On completion of addition, the mixture is left to react for 0.5 hour at 30° C. and the mixture is then cooled to −5° C. A solution containing 5.6 g (50 mmol) of potassium tert-butoxide and 50 ml of anhydrous tetrahydrofuran is added at this temperature: the mixture rams violet in color and then a precipitate forms. The mixture is left to react for 0.5 hour at 0° C. and then 8.5 g (60 mmol) of methyl iodide are added. The mixture is left to react for 1 hour at room temperature. The mixture is diluted with 200 ml of ethyl acetate. The mixture is washed 2 times with 150 ml of water on each occasion. The solution is dried over magnesium sulfate and then treated with active charcoal. The solution is concentrated: a purplish-brown honey-like product is obtained which is crystallized from 50 ml of ether. The precipitate is washed and then dried under vacuum. A second crop of product is recovered after concentrating the mother liquors and taking up the residual honey-like product in 50 ml of diisopropyl ether. 12 g (yield=77%) of 4-methyl-2-methylthio-4-phenyl-1-phenylamino-2-imidazolin-5-one (Compound 9) are thus obtained in the form of a beige powder melting at 149° C.

By carrying out the preparations as above, the following compounds were obtained:

| No. | $R'_1$ | $R_2$ | $R_3$ | B | $R_4$ | M.p. |
|---|---|---|---|---|---|---|
| 58 | — | Me | Me | NH | 2,3-$(Me)_2$Ph | 116° C. |
| 67 | — | Me | Me | $(CH_2)_2$ | Ph | honey-like consistency |
| 76 | — | Me | Me | $CH_2$ | 3-pyridyl | 67° C. |
| 77 | — | Me | Me | $CH_2$ | 2-pyridyl | honey-like consistency |
| 78 | — | Me | Me | N | PhCH= | 95° C. |
| 83 | 4-Me | Me | Me | NH | Ph | 179° C. |
| 84 | — | Me | Me | NH | 3-Me-2-pyridyl | 148° C. |
| 85 | 4-Cl | Me | Me | NH | Ph | 173° C. |
| 86 | 3,4-$(MeO)_2$ | Me | Me | NH | Ph | 165° C. |
| 87 | 3,4-$(MeO)_2$ | Me | Me | NH | 2-Me—Ph | 151° C. |
| 88 | 4-Me | Me | Me | NH | 2-Me—Ph | 52° C. |
| 89 | 4-PhO | Me | Me | NH | Ph | 146° C. |
| 90 | 4-Cl | Me | Me | NH | 3-Me-2-pyridyl | 133° C. |
| 91 | 4-Cl | Me | Me | NH | 2-pyridyl | 172° C. |
| 93 | 4-PhO | Me | Me | NH | 2-Me—Ph | 130° C. |
| 94 | 4-F | Me | Me | NH | 2-Me—Ph | 120° C. |
| 96 | 4-Cl | Me | Me | NH | 2-Cl—Ph | 145° C. |
| 99 | 4-Cl | H | Me | NH | 4-Cl—Ph | 163° C. |
| 100 | 4-Cl | Me | Me | NH | 4-Cl—Ph | 172° C. |
| 101 | 4-Cl | Me | Me | NH | 4-F—Ph | 170° C. |
| 102 | 4-Cl | Me | Me | NH | 3-Cl—Ph | 146° C. |
| 103 | 4-Cl | Me | Me | NH | 4-Me—Ph | 178° C. |
| 105 | 4-Cl | Me | Me | NH | 2-Me—Ph | 124° C. |
| 106 | 4-Cl | Me | Me | NH | 3-Me—Ph | 136° C. |
| 107 | 4-F | Me | Me | NH | 3-Me—Ph | 121° C. |
| 108 | — | Me | Me | NH | 3-F—Ph | 163° C. |
| 109 | — | Me | Me | NH | 2,5-$F_2$—Ph | 141° C. |
| 110 | 4-Me | Me | Me | NH | 4-Cl—Ph | 168° C. |
| 111 | 4-Me | Me | Me | NH | 2-Cl—Ph | 168° C. |
| 114 | 4-Me | Me | Me | NH | 3-Cl—Ph | 184° C. |
| 115 | 4-F | Me | Me | NH | 3-Cl—Ph | 124° C. |
| 116 | 4-Me | Me | Me | NH | 4-F—Ph | 186° C. |
| 117 | 4-Me | Me | Me | NH | 4-Me—Ph | 157° C. |
| 118 | 4-F | Me | Me | NH | 4-Me—Ph | 158° C. |
| 119 | 4-Me | Me | Me | NH | 3-Me—Ph | 178° C. |
| 121 | 4-F | Me | Me | NH | 4-Cl—Ph | 159° C. |
| 122 | — | Me | Me | NH | 2,4-$(Me)_2$—Ph | 63° C. |
| 123 | — | Me | Me | NH | 3-Cl-2-Pyr | 127° C. |
| 124 | 4-Cl | Me | Me | NH | 2-F—Ph | 120° C. |
| 125 | 4-F | Me | Me | NH | 2-F—Ph | 112° C. |
| 126 | 4-Me | Me | Me | NH | 2-F—Ph | 156° C. |

Also prepared in this manner were the following:

Compound 92, melting at 166° C. and having the formula:

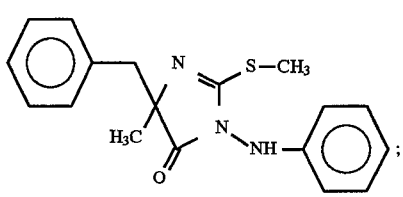

Compound 97, melting at 158° C. and having the formula:

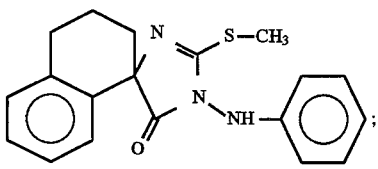

Compound 98, melting at 85° C. and having the formula:

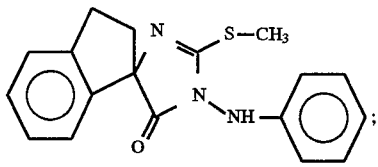

Compound 104, melting at 168° C. and having the formula:

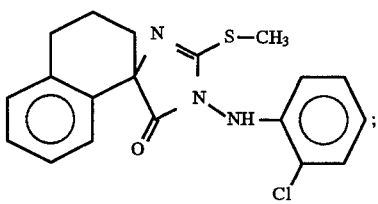

Compound 112, melting at 191° C. and having the formula:

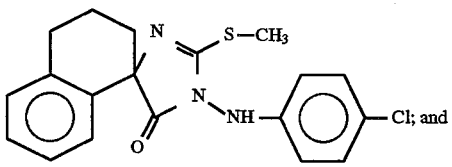

Compound 113, melting at 174° C. and having the formula:

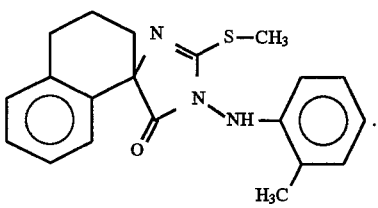

Example 11

Preparation of 4-phenyl-4-methyl-1-(phenylthio)-2-methylthio-2-imidazolin-5-one (Compound 95: M.p. 112° C.):

0.6 g (2.7 mmol) of 2-methylthio-4-methyl-4-phenyl-2-imidazolin-5-one in solution in 50 ml of anhydrous tetrahydrofuran (THF) is charged to a 100 ml, three-necked, round-bottomed flask under an inert atmosphere. The solution is stirred with a magnetic stirrer and is cooled to 0° C. (ice bath+acetone). 0.30 g (1 molar equivalent) of potassium tert-butoxide is added and the mixture is stirred for 10 minutes at 0° C. A solution containing 0.40 g of phenylsulfenyl chloride (phenylthio chloride) and 10 ml of anhydrous THF is then run in. The mixture is then left to return to room temperature for one hour. The reaction mixture is run into 100 ml of water. Extraction is carried out with 100 ml of ethyl acetate. The organic phase is washed 4 times with water and dried over sodium sulfate.

The organic phase is concentrated under vacuum. A yellow honey-like product is obtained which crystallizes from isopropyl ether after purification on silica with a yield of 68% (melting point: 112° C.).

EXAMPLES OF THE PREPARATION OF COMPOUNDS OF FORMULA (I') AND INTERMEDIATES THERETO

In the tables below, the methyl, ethyl, propyl, butyl and phenyl radicals are represented respectively by Me, Et, Pr, Bu and Ph, and M.p. means melting point.

Example 12

Preparation of a hydrazide (XV) according to Process B(4) (a): Preparation of 2-propionylamino-2-phenyl-2'-phenylpropionohydrazide (Compound 302):

4.51 g (0.0278 mol) of N,N'-carbonyldiimidazole are added to a solution, stirred under an inert atmosphere, of 5.6 g (0.0253 mol) of N-propionyl-2-methyl-2-phenylglycine in 150 ml of anhydrous dichloromethane and the mixture is allowed to react until gas evolution has ceased. 3.28 g (0.0304 mol) of phenylhydrazine are then added and the mixture is allowed to react for 12 hours. The reaction mixture is then concentrated under reduced pressure and the residue obtained in chromatographed on 400 g of $SiO_2$, the eluent being an ethyl acetate/heptane (65%/35%) mixture. The advantageous fractions are then concentrated under reduced pressure. 4.80 g (0.0154 mol) of 2-propionylamino-2-phenyl-2'-phenylpropionohydrazide, melting at 144° C., are thus recovered with a yield of 61%.

By carrying out the reaction according to the same procedure, Compounds 301 to 309 and 312, collated in the following table, are obtained, which are intermediates of Compounds 201 to 209 and 212:

$$R_{30}-\underset{O}{\underset{\|}{C}}-NH-\underset{CH_3}{\underset{|}{\overset{R_1}{\underset{|}{C}}}}-\underset{O}{\underset{\|}{C}}-NH-NH-R_{40}$$

| No. | $R_1$ | $R_{30}$ | $R_{40}$ | Yield (%) | M.p. |
|---|---|---|---|---|---|
| 301 | Ph | Me | Ph | 53 | 150° C. |
| 302 | Ph | Et | Ph | 61 | 144° C. |
| 303 | Ph | $CF_3$ | Ph | 50 | 161° C. |
| 304 | Ph | $CCl_3$ | Ph | 49 | 187° C. |

-continued $$R_{30}-\underset{\underset{O}{\|}}{C}-NH-\underset{\underset{CH_3}{|}}{C}-\underset{\underset{O}{\|}}{C}-NH-NH-R_{40}$$

| No. | R₁ | R₃₀ | R₄₀ | Yield (%) | M.p. |
|---|---|---|---|---|---|
| 305 | Ph | nPr | Ph | 55 | 102° C. |
| 306 | Ph | iPr | Ph | 45 | 130° C. |
| 307 | Ph | tBu | Ph | 77 | 134° C. |
| 308 | 4-Cl—Ph | Me | Ph | 71 | 180° C. |
| 309 | 4-Cl—Ph | Me | 2-Me—Ph | 64 | 152° C. |
| 312 | Ph | ClCH₂ | Ph | 55 | 146° C. |

Example 13

Preparation of a hydrazide (XV) according to Process B(4) (b): Preparation of phenylhydrazide of N-trifluoroacetyl-2-(4-methylphenyl)glycine:

1.38 g (5 mmol) of N-trifluoroacetyl-2-(4-methylphenyl) glycine, 25 ml of anhydrous toluene and then 0.75 ml (5.5 mmol) of anhydrous triethylamine are introduced into a 100 ml round-bottomed flask. The reaction mixture is cooled to −15° C. and then 0.475 ml (5 mmol) of ethyl chloroformate is run in dropwise. A white precipitate is then formed and stirring is continued at −10° C. for 30 minutes.

0.5 g (4.5 mmol) of phenylhydrazine and 25 ml of anhydrous toluene are introduced into a vacuum flask and the mixture is cooled to −15° C.

The contents of the first round-bottomed flask are rapidly filtered through sintered glass into the Erlenmeyer flask containing the phenylhydrazine. The reaction mixture is allowed to return to room temperature, washed with dilute sodium hydroxide solution and water, and then dried over MgSO₄ before filtering and evaporating. 1.4 g (78% yield) are thus obtained of a white solid having a melting point equal to 162° C. and having the formula:

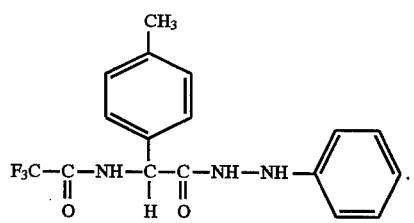

Example 14

Preparation of the compounds of formula (I'a) according to Process B, by Cyclization of compounds of formula (XV): Preparation of 2,4-dimethyl-4-phenyl-1-phenylamino-2-imidazolin-5-one (Compound 201 ):

A stirred solution of 1.5 g (0.005 mol) of 2-acetylamino-2-phenyl-2'-phenylpropionohydrazide and of 0.17 g (0.001 mol) of paratoluenesulfonic acid in 25 ml of toluene is held at reflux for 7 hours, the water being removed as it is formed. The reaction mixture is then concentrated under reduced pressure and the residue obtained is chromatographed on 200 g of SiO₂, the eluent being an ethyl acetate/heptane (50%/50%) mixture. A thick oil is isolated which crystallizes by triturating with diisopropyl ether. After filtration, 0.5 g (0.0018 mol) of 2,4-dimethyl-4-phenyl-1-phenylamino-2-imidazolin-5-one (Compound 201) is recovered with a yield of 36% in the form of a white powder melting at 135° C.

Compounds 201 to 209 and 212 of the formula

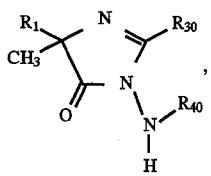

recorded in the following table, are prepared according to the same procedure with the appropriate reactants.

| No. | R₁ | R₃₀ | R₄₀ | Yield (%) | M.p. |
|---|---|---|---|---|---|
| 201 | Ph | Me | Ph | 36 | 135° C. |
| 202 | Ph | Et | Ph | 86 | honey |
| 203 | Ph | CF₃ | Ph | 66 | 104° C. |
| 204 | Ph | CCl₃ | Ph | 14 | 68° C. |
| 205 | Ph | nPr | Ph | 84 | honey |
| 206 | Ph | iPr | Ph | 69 | 122° C. |
| 207 | Ph | tBu | Ph | 11 | 87° C. |
| 208 | 4-Cl—Ph | Me | Ph | 54 | 140° C. |
| 209 | 4-Cl—Ph | Me | 2-Me—Ph | 65 | 142° C. |
| 212 | Ph | ClCH₂ | Ph | 79 | 76° C. |
| 214 | Ph | Et | Ph | 53 | 78° C. |
| 215 | Ph | Et | 2-Me—Ph | 68 | 107° C. |
| 216 | Ph | Me | 2-Me—Ph | 53 | 180° C. |
| 218 | Ph | MeOCH₂ | Ph | 8 | 95° C. |
| 219 | Ph | MeOCH₂ | 3-Cl—Ph | 20 | 125° C. |
| 226 | 4-Me—Ph | Me | Ph | 41 | 142° C. |
| 229 | Ph | MeOCH₂ | 2-Me—Ph | 54 | 122° C. |
| 233 | 4-Me-Ph | CF₃ | Ph | 35 | 166° C. |
| 245 | Ph | MeOCH₂ | 2,3-diMe—Ph | 55 | 91° C. |

Example 15

Preparation of a compound of formula (I'a) according to Process C(1): 2,4-dimethyl-4-phenyl-1-phenylamino-2-imidazolin-5-one (Compound 201):

A solution containing 0.9 g (4 mmol) of 2,4-dimethyl-4-phenyl-2-oxazolin-5-one, 0.43 g (4 mmol) of phenylhydrazine and 0.1 g of paratoluenesulfonic acid in 30 ml of toluene is heated at reflux for one hour. The water formed is removed by azeotropic entrainment and the mixture is concentrated under reduced pressure. The crude product is then purified by chromatography on silica gel.

Compound 201 is thus obtained with a yield of 25%.

According to the same procedure, 2,4-dimethyl-4-(4-chlorophenyl)-1-(2,3-dimethylphenylamino)-2-imidazolin-5-one (Compound 210) is obtained with a yield of 18% (M.p.: 164° C.).

Example 16

Preparation of a compound of formula (I'a) according to Process C(2): 2,4-dimethyl-4-(4-chlorophenyl)-1-(2-chlorophenylamino)-2-imidazolin-5-one (Compound 211):

A solution containing 1.5 g (6.7 mmol) of 2,4-dimethyl-4-(4-chlorophenyl)-2-oxazolin-5-one, 0.93 g (6.7 mmol) of 2-chlorophenylhydrazine and 0.25 g of sodium acetate in 20 ml of acetic acid is heated at reflux for 2 hours. The mixture is concentrated under reduced pressure and the residues dissolved in 150 ml of methylene chloride. The methylene chloride solution is washed with an aqueous bicarbonate solution and then with pure water. The solution is concentrated and the product purified by chromatography on silica gel, the eluent being an ethyl acetate/heptane (30%/70%) mixture.

Compound 211 is thus obtained with a yield of 43%.

Compound 213 is obtained according to the same procedure with a yield of 33.5%.

The compounds of the formula:

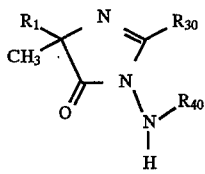

are obtained according to the same procedure, which compounds are collated in the following table:

| No. | $R_1$ | $R_{30}$ | $R_{40}$ | Yield (%) | M.p. |
|---|---|---|---|---|---|
| 213 | 4-Br—Ph | Me | Ph | 34 | 147° C. |
| 217 | 4-Cl—Ph | Ph | 3-Cl—Ph | 31 | 120° C. |
| 220 | Ph | Me | 3-Cl—Ph | 43 | 163° C. |
| 221 | 4-Cl—Ph | Et | Ph | 27 | 144° C. |
| 222 | 4-Br—Ph | Me | 2-Me—Ph | 38 | 144° C. |
| 223 | 4-Br—Ph | Me | 2-Cl—Ph | 41 | 145° C. |
| 224 | 4-Br—Ph | Et | Ph | 20 | 110° C. |
| 225 | 4-Cl—Ph | Me | iPr | 53 | honey |
| 230 | 4-F—Ph | Me | Ph | — | 150° C. |
| 231 | PhCH$_2$ | Me | Ph | — | 192° C. |
| 232 | PhCH$_2$ | Et | Ph | — | 167° C. |
| 234 | Ph | Me | 4-iPr—Ph | 20 | 162° C. |
| 235 | Ph | Me | 2,3-diMe—Ph | 16 | 64° C. |
| 236 | Ph | Me | 2,3-diCl—Ph | 33 | 165° C. |
| 237 | Ph | Me | 2,4-diMe—Ph | 43 | 100° C. |
| 238 | Ph | Me | 3,4-diMe—Ph | 30 | 135° C. |
| 239 | Ph | Me | 4-Cl—Ph | 56 | 69° C. |
| 240 | Ph | Me | 2-Cl—Ph | 50 | 196° C. |
| 241 | Ph | Me | 4-MePh | 34 | 142° C. |
| 242 | Ph | Me | 2-MePh | 45 | 129° C. |
| 243 | Ph | Et | 3-Cl—Ph | 26 | 82° C. |
| 244 | Ph | Et | 2,3-diCl—Ph | 41 | 60° C. |
| 246 | Ph | Et | 3,4-diMe—Ph | 32 | 94° C. |
| 247 | Ph | Et | 2,3-diMe—Ph | 27 | 109° C. |
| 248 | Ph | Et | 2,4-diMe—Ph | 50 | 45° C. |
| 249 | Ph | Et | 4-Cl—Ph | 48 | 73° C. |
| 250 | Ph | Et | 4-iPr—Ph | 16 | 73° C. |
| 251 | Ph | Et | 2-Cl—Ph | 56 | 84° C. |
| 252 | Ph | Et | 3-Me—Ph | 14 | 85° C. |
| 253 | 4-PhO—Ph | Me | Ph | 54 | 134° C. |
| 256 | 4-PhO—Ph | Et | Ph | 58 | honey |
| 259 | 3-Cl—Ph | Et | Ph | 49 | 117° C. |

Likewise, the spiro Compounds 227 (yield 56%, M.p.: 203° C.) and 228 (yield 56%, M.p.: 153° C.) of formulae:

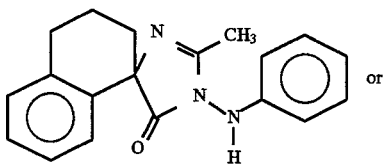

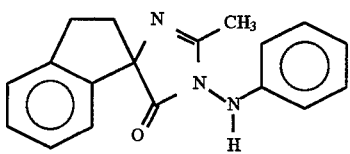

are obtained.

Example 17

Preparation according to Process E of compounds of formula (I'a), in which $R_{30}$ is a hydrogen atom, and of their intermediates of formula (XVI):

Part (a): 4.58 g (0.0208 mol) of methylphenylglycine acid chloride hydrochloride are added, in a single step, to a solution of 2.25 g (0.0208 mol) of phenylhydrazine in 50 ml of diethyl ether and the suspension thus formed is left stirring for 18 hours. The suspension is filtered and the solid is sucked dry and then redissolved in distilled water. The solution obtained is slowly basified to pH=7–8 using a saturated sodium hydrogen carbonate solution. The precipitate thus formed is filtered and washed with distilled water and then recrystallized from isopropanol. After filtering the crystals and drying under reduced pressure at 50° C., 2 g (0.0078 mol) of (2R,2S)-2-amino-2-phenyl-2'-phenylpropionohydrazide (Compound 355), melting at 154° C. are recovered, i.e. with a yield of 38%.

The phenylpropionohydrazides of the formula:

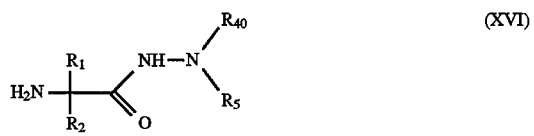

(XVI)

were obtained according to the same procedure, which compounds are recorded in the following table:

| No. | $R_1$ | $R_2$ | $R_{40}$ | $R_5$ | Yield (%) | M.p. |
|---|---|---|---|---|---|---|
| 355 | Ph | Me | Ph | H | 38 | 154° C. |
| 357 | Ph | Me | 2-Me—Ph | H | 32 | 115° C. |
| 358 | Ph | Me | 3-Cl—Ph | H | 20 | 164° C. |
| 360 | Ph | Me | 2-Cl—Ph | H | 68 | 112° C. |
| 361 | Ph | Me | 4-Cl—Ph | H | 48 | 177° C. |
| 363 | Ph | Me | 2-F—Ph | H | 43 | 112° C. |
| 364 | Ph | Me | 4-F—Ph | H | 40 | 142° C. |
| 365 | Ph | Me | 3-Me—Ph | H | 45 | 110° C. |
| 366 | Ph | Me | 4-Me—Ph | H | 26 | 168° C. |
| 367 | Ph | Me | 3-F—Ph | H | 33 | 161° C. |

Likewise, the spiro Compound 362 [$R_1=C_6H_4$, $R_2=(CH_2)_2$, $R_3=H$, $R_4=Ph$; yield 7%, M.p.: 171° C.] is obtained.

Part (b): (4R,4S)4-(4-fluorophenyl)-4-methyl1-phenylamino-2-imidazolin-5-one (Compound 254):

A solution of 2.73 g (0.01 mol) of (2R,2S)-2-amino-2-(4-fluorophenyl)-2'-phenylpropionohydrazide in 16 ml of N,N-dimethylformamide dimethyl acetal is stirred for 48 hours. The reaction mixture is concentrated under reduced pressure. The residue obtained is then chromatographed on silica, the eluent being an n-heptane/ethyl acetate mixture in the proportion: 50/50. The fractions containing the pure Compound 254 are concentrated together under reduced pressure. 1.5 g (0.0053 mol) of (4R,4S)-4-(4-fluorophenyl)-4-methyl-1-phenylamino-2-imidazolin-5-one, melting at 140° C. on a Kofler-type bench, are thus recovered, i.e. a yield of 53%.

The compounds of formula (I'a), in which $R_{30}$ is a hydrogen atom, that is to say, compounds of the formula:

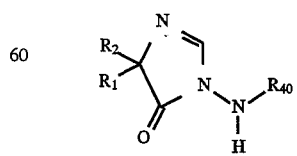

were obtained according to this procedure, which compounds are collated in the following table:

| No. | $R_1$ | $R_{30}$ | $R_{40}$ | Yield (%) | M.p. |
|---|---|---|---|---|---|
| 254 | 4-F—Ph | Me | Ph | 53 | 140° C. |
| 255 | Ph | Me | Ph | 38 | 129° C. |
| 257 | Ph | Me | 2-Me—Ph | 72 | 175° C. |
| 258 | Ph | Me | 3-Cl—Ph | 46 | 177° C. |
| 260 | Ph | Me | 2-Cl—Ph | 79 | 176° C. |
| 261 | Ph | Me | 4-Cl—Ph | 33 | 153° C. |
| *262 | $C_6H_4$ | $(CH_2)_2$ | Ph | 64 | 202° C. |
| 263 | Ph | Me | 2-F—Ph | 86 | 151° C. |
| 264 | Ph | Me | 4-F—Ph | 40 | 124° C. |
| 265 | Ph | Me | 3-Me—Ph | 50 | 109° C. |
| 266 | Ph | Me | 4-Me—Ph | 41 | 127° C. |
| 267 | Ph | Me | 3-F—Ph | 20 | 137° C. |

*spiro compound

EXAMPLE OF THE PREPARATION OF COMPOUNDS OF FORMULA (I")

In the table below, the methyl, ethyl, propyl, pyridyl, acetyl and phenyl radicals are respectively represented by Me, Et, Pr, Py, Ac and Ph, and M.p. means melting point.

Example 18

Preparation of Compound 402:

1.4 g (1.74 mmol) of sodium in 60 ml of ethanol is reacted, under a dry nitrogen atmosphere, in a 100 ml 3-necked flask. 4 g (1.28 mmol) of 4-methyl-2-methylthio-4-phenyl-1-phenylamino-2-imidazolin-5-one are then added. The mixture is refluxed for 6 hours, then cooled to ambient temperature and acidified with 0.4 ml of acetic acid. The mixture is diluted with 300 ml of ethyl acetate. The organic solution is washed with water, then dried over magnesium sulfate and concentrated under reduced pressure: a brownish red syrup is obtained. The product is purified by chromatography on a silica column. 1.25 g (31% yield) of Compound 402 is obtained in the form of a slightly pinkish powder melting at 106° C.

In the same manner, the compounds of the formula

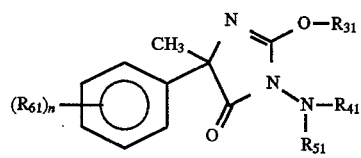

described below have been prepared:

| No. | $(R_{61})_n$ | $R_{31}$ | $R_{41}$ | $R_{51}$ | M.p. (°C.) |
|---|---|---|---|---|---|
| 401 | — | Me | Ph | H | 149 |
| 402 | — | Et | Ph | H | 106 |
| 403 | — | nPr | Ph | H | 80 |
| 404 | 4-Cl | Me | Ph | H | 140 |
| 405 | — | Me | 2-Me—Ph | H | 118 |
| 406 | 4-Cl | Me | 2-pyridyl | H | 150 |
| 408 | — | Me | 2-Cl—Ph | H | 94 |
| 409 | — | Me | 4-Cl—Ph | H | 124 |
| 411 | 3,4-di(MeO) | Me | Ph | H | 150 |
| 412 | 4-Cl | Me | 4-Cl—Ph | H | 176 |
| 413 | 4-Cl | Me | 4-F—Ph | H | 147 |
| 414 | 4-Cl | Me | 2-Cl—Ph | H | syrup |
| 415 | 4-Cl | Me | 3-Cl—Ph | H | 147 |
| 416 | 4-Cl | Me | 4-Me—Ph | H | 162 |
| 417 | 4-Cl | Me | 3-Me—Ph | H | 116 |
| 418 | 4-Me | Me | Ph | H | 110 |
| 419 | 4-F | Me | Ph | H | 104 |
| 420 | 4-Cl | Me | 2-Me—Ph | H | syrup |
| 421 | 4-F | Me | 3-Me—Ph | H | 114 |
| 423 | 4-F | Me | 2-Me—Ph | H | 88 |
| 424 | 4-Me | Me | 4-Cl—Ph | H | 166 |
| 425 | 4-Me | Me | 3-Cl—Ph | H | 155 |
| 427 | 4-Me | Me | 2-Cl—Ph | H | 86 |
| 428 | 4-Me | Me | 4-F—Ph | H | 124 |
| 429 | 4-F | Me | 3-Cl—Ph | H | 160 |
| 430 | 4-Me | Me | 4-Me—Ph | H | 155 |
| 431 | 4-F | Me | 4-Me—Ph | H | 149 |
| 432 | 4-Me | Me | 2-Me—Ph | H | 128 |
| 433 | — | Me | 3-F—Ph | H | 121 |
| 434 | 4-Me | Me | 3-Me—Ph | H | 138 |
| 435 | 4-PhO | Me | 2-Me—Ph | H | 120 |
| 436 | 4-F | Me | 4-Cl—Ph | H | 142 |
| 437 | — | Me | 4-F—Ph | H | 157 |
| 438 | — | Me | 2,4-di(F)—Ph | H | 166 |
| 439 | — | Me | 4-Me—Ph | H | 116 |
| 440 | 4-F | Me | 2-F—Ph | H | syrup |
| 441 | 4-Me | Me | 2-F—Ph | H | 90 |
| 442 | 4-Cl | Me | 2-F—Ph | H | syrup |
| 443 | 4-F | Me | 2-Cl—Ph | H | syrup |
| 444 | — | Me | 2,3-di(Me)—Ph | H | 140 |
| 445 | — | Me | 3-Cl-2-pyridyl | H | 140 |
| 446 | — | Me | 3-Me—Ph | H | 54 |
| 447 | — | Me | 2-F—Ph | H | 136 |
| 448 | — | Me | 3-Cl—Ph | H | 93 |
| 449 | 4-F | Me | 3-Me-2-pyridyl | H | 126 |
| 450 | 4-F | Me | 3-F—Ph | H | 120 |
| 451 | 4-Cl | Me | 3-F—Ph | H | 125 |
| 452 | 3-Cl | Me | Ph | H | 155 |
| 453 | 3-Cl | Me | 3-Me—Ph | H | 100 |
| 454 | 3-Cl | Me | 3-Cl—Ph | H | 105 |
| 455 | 3-Cl | Me | 3-F—Ph | H | 135 |
| 456 | 3-Cl | Me | 2-Me—Ph | H | 116 |
| 457 | 3-F | Me | Ph | H | 134 |
| 458 | 3-F | Me | 3-F—Ph | H | 115 |
| 459 | — | Me | Ph | Ac | 121 |
| 460 | 3-F | Me | 3-Cl—Ph | H | 90 |
| 461 | 3-Me | Me | Ph | H | 98 |
| 462 | 3-Me | Me | 3-F—Ph | H | 118 |
| 463 | 4-PhO | Me | 2-pyridyl | H | 146 |
| 464 | 2,4-diF | Me | Ph | H | 163 |
| 465 | 2,4-diF | Me | 3-F—Ph | H | 162 |
| 466 | 4-PhO | Me | Ph | H | 114 |
| 467 | 4-PhO | Me | 3-F—Ph | H | 56 |
| 468 | 2-Cl | Me | Ph | H | 214 |
| 469 | — | Me | 4-PhO—Ph | H | 118 |
| 470 | 2-Cl | Me | 3-F—Ph | H | 201 |
| 471 | 2-F | Me | Ph | H | 172 |
| 472 | 2-F | Me | 3-F—Ph | H | 151 |
| 473 | 2,4-diF | Me | 3-Cl—Ph | H | 130 |
| 474 | 2-F | Me | 3-Cl—Ph | H | 151 |
| 475 | 4-iPr | Me | Ph | H | 132 |
| 476 | 4-PhO | Me | 3-Me-2-pyridyl | H | 142 |
| 477 | 4-iPr | Me | 3-F—Ph | H | 128 |
| 478 | 3-Me | Me | 3-Cl—Ph | H | 115 |
| 479 | 4-iPr | Me | 3-Cl—Ph | H | 139 |
| 480 | 4-Br | Me | Ph | H | 138 |
| 481 | 4-$NO_2$ | Me | Ph | H | 143 |
| 482 | 3-PhO | Me | Ph | H | syrup |
| 483 | 2,4-di(F)-4-PhO | Me | 3-F—Ph | H | 71 |
| 484 | 2,4-di(F)-4-PhO | Me | Ph | H | 76 |
| 485 | 4-F-4-PhO | Me | Ph | H | 91 |

Compound 407:

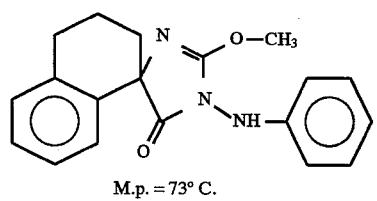

M.p. = 73° C.

Compound 410:

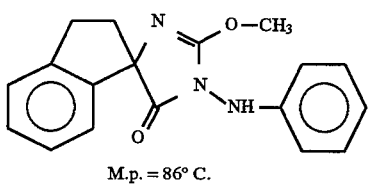

M.p. = 86° C.

Compound 422:

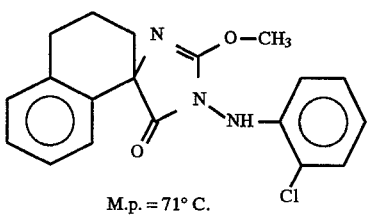

M.p. = 71° C.

Compound 486:

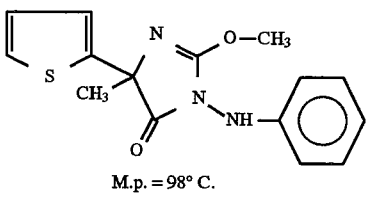

M.p. = 98° C.

EXAMPLES OF THE PREPARATION OF COMPOUNDS OF FORMULA (I''') AND INTERMEDIATES THERETO

The Examples below illustrate the optically active derivatives of formula (I''') and their process of preparation.

The structures of all of the derivatives illustrated were characterized using at least one of the spectral techniques noted hereinabove, as well as the usual methods for measuring optical rotations. The enantiomeric excesses were determined either by chiral phase high performance liquid chromatography or by NMR.

In the tables below, the phenyl, methyl and ethyl radicals are represented by Ph, Me and Et respectively. The abbreviation "c" used in connection with optical rotation values refers to the concentration of the compound in the sample measured, expressed as grams per 100 ml of solvent.

Example 19

Preparation of (+)-(4S)-4-methyl-2-methylthio-4-phenyl-1-phenylamino-2-imidazolin-5-one (Compound 501):

682 g (3.08 mol) of methyl (+)-(2S)-2-phenyl-2-(isothiocyanato)propionate, dissolved in 4 liters of anhydrous tetrahydrofuran, are introduced into a 20 liter reactor through which passes a stream of argon. Cooling is carried out to 15° C. 343 g (3.08 mol) of phenylhydrazine, dissolved in 2 liters of tetrahydrofuran, are run in over 30 minutes, the temperature being maintained between 15° C. and 18° C. The mixture is kept stirring for 40 minutes and then cooled to 0° C. A solution of 346 g (3.08 mol) of potassium tert-butoxide in 4 liters of tetrahydrofuran is nm in over 1 hour, the temperature being maintained at 0° C. The mixture is stirred for a further 2 hours at 0° C. and the formation of a pale-pink precipitate is observed. 218 ml (3.39 mol) of methyl iodide are run in over 15 minutes, the temperature being maintained between 0° C. and 3° C., and the temperature is then allowed to rise to room temperature while continuing to stir for 2 hours. The reaction mixture is poured onto 5 liters of water. After separating, the aqueous phase is extracted with 3 times 3 liters of ethyl acetate. The combined organic phases are washed with 5 liters of water, dried over magnesium sulfate and the concentrated under reduced pressure. 1099 g of a brown solid are obtained. The latter is recrystallized from 2 liters of toluene.

There are obtained, after drying, 555 g of (+)-(4S)-4-methyl-2-methylthio-4-phenyl-1-phenylamino-2-imidazolin-5-one in the form of an off-white solid melting at 138° C.; yield=58%; $[\alpha]_D^{27°\ C.}$=+61.1° (+ or –2.9°) (c=0.86 in ethanol); degree of enantiomeric excess (e.e)>98%.

In the same way, the following analogous compounds of formula (I'''c) were obtained:

(I'''c)

| Compound No. | $R_{42}$ | $R_{62}$ | $[\alpha]_D$ (c) Solvent | M.p. (°C.) | Yield (%) |
|---|---|---|---|---|---|
| 501 | Ph | H | +61° (0.8) EtOH | 138 | 58 |
| 511 | Ph | 4-F | +53° (0.7) EtOH | 114 | 60 |
| 512 | Ph | 4-F | (–) | 114 | 66 |
| 513 | 3-FPh | 4-F | +52° (0.7) EtOH | 130 | 70 |
| 514 | 3-FPh | 4-F | (–) | — | — |
| 515 | Ph | 4-(4-FPh)O | (+) | 138 | 45 |
| 516 | Ph | 4-(4-FPh)O | 13° (0–4) EtOH | 139 | 71 |

Example 20

Preparation of (+)-(4S)-4-methyl-4-phenyl-1-phenylamino-2-thiohydantoin (Compound 507):

0.7 g (0.00316 mol) of methyl (+)-(2S)-2-isothiocyanato-2-phenylpropionate, diluted in 15 ml of dry tetrohydrofuran, is introduced into a 100 ml three-necked flask under a dry nitrogen atmosphere. 0.32 ml (0.00316 mol) of phenylhydrazine, diluted in 5 ml of tetrohydrofuran, is run in at 20° C. in a single step. The temperature rises by 2° C. The medium is kept magnetically stirring for 30 minutes. A dark-beige precipitate appears. The medium is neutralized with 0.4 ml of acetic acid and then treated with 20 ml of water. After separating, the aqueous phase is extracted with 3 times 20 ml of ethyl ether. The organic phases are combined, washed with 2 times 30 ml of water, dried over magnesium sulfate and then concentrated under reduced pressure. The solid residue obtained is chromatographed on a silica column, using an eluent mixture composed of heptane and ethyl acetate in the proportions of 50/50.

0.55 g of (+)-(4S)-4-methyl-4-phenyl-1-phenylamino-2-thiohydantoin is collected in the form of a beige solid melting at 167° C.; yield =58%; $[\alpha]_D^{27°\ C.}$=+86° (+ or –3.2° ) (c=0.8 in methanol).

Example 21

Preparation of methyl (+)-(2S)-2-isothiocyanato-2-phenylpropionate (Compound 508):

780 g (3.61 mol) of methyl (+)-(2S)-2-amino-2-phenylpropionate hydrochloride and then 3.4 liters of water are introduced into a 20 liter reactor. The temperature is brought to 20° C. 3.4 liters of toluene are added and then 911 g (10.8 mol) of sodium hydrogencarbonate are added portionwise over 1 hour. The temperature falls to 8°–9° C. 276 ml (3.61 mol) of thiophosgene are run in over 2 hours. The reaction is accompanied by an evolution of gas and by a rise in temperature, which reaches 24° C. at the end of the addition. The medium is kept stirring for a further 2 hours. After separating, the aqueous phase is extracted with 2 liters of toluene. The combined toluene phases are washed with 4 liters of water and then dried over magnesium sulfate. The solution is concentrated under reduced pressure.

There are obtained 682 g of methyl (+)-(2S)-2-isothiocyanato-2-phenylpropionate in the form of a slightly colored oil; yield=85%; $[\alpha]_D^{27°\ C.}=+16°$ (+ or −6.4°) (c=0.78 in chloroform).

In the same way, the following analogous compounds of formula (XIXa) were obtained:

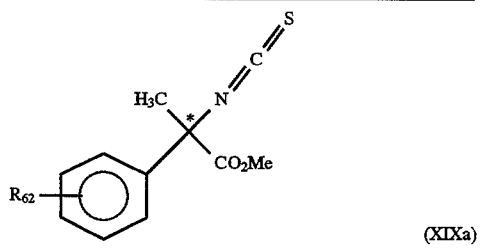

(XIXa)

| Compound No. | R$_{62}$ | $[\alpha]_D$ (c) Solvent | Physical State | Yield (%) |
|---|---|---|---|---|
| 508 | H | +16° (0.78) CHCl$_3$ | Oil | 85 |
| 517 | 4-F | (+) | Oil | 72 |
| 518 | 4-F | (−) | Oil | 80 |
| 519 | 4-(4-FPh)O | (+) | Oil | 61 |
| 520 | 4-(4-FPh)O | −11° (0.7) EtOH | Oil | 70 |

Example 22

Preparation of methyl (+)-(2S)-2-amino-2-phenylpropionate hydrochloride (Compound 509):

611 g (3.7 mol) of (+)-2-aminophenylpropionic acid are charged to a 10 liter reactor, to which 5 liters of methanol are added. 819 ml (11.22 mol) of thionyl chloride are nm onto the white suspension formed over 2 hours. The temperature reaches 58° C. at the end of the addition. A significant evolution of gas is observed, which gas is trapped by a dilute sodium hydroxide solution. The medium is heated at 65° C. for 14 hours. The solution is then concentrated under reduced pressure. The solid obtained is treated with 1 liter of toluene, filtered and then dried under vacuum. There are obtained 762 g of methyl (+)-(2S)-2-amino-2-phenylpropionate hydrochloride in the form of a white powder melting at 162° C.; yield=62%; $[\alpha]_D^{29°\ C.}=+53.3°$ (+ or −3.3°) (c=0.75 in water).

In the same way, the following analogous compounds of formula (XXIIa) were obtained:

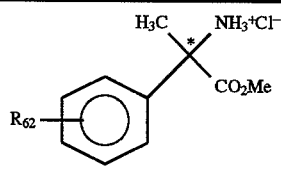

(XXIIa)

| Compound No. | R$_{62}$ | $[\alpha]_D$ (c) Solvent | Physical State | M.p. (°C.) | Yield (%) |
|---|---|---|---|---|---|
| 509 | H | +54° (0.91) CHCl$_3$ | white crystals | 162 | 62 |
| 521 | 4-F | +61° (0.9) EtOH | white solid | 50–60 | 93 |
| 522 | 4-F | (−) | white solid | — | 95 |
| 523 | 4-(4-FPh)O | (+) | white solid | — | 87 |
| 524 | 4-(4-FPh)O | (−) | white solid | — | 95 |

Methyl (+)-(2S)-2-amino-2-phenylpropionate is obtained by treating the hydrochloride prepared above with one equivalent of sodium hydrogencarbonate and then extracting with dichloromethane. It exists in the form of a colorless, slightly viscous oil; $[\alpha]_D^{29°\ C.}=+54.8°$ (+ or −2.7°) (c=0.91 in chloroform), e.e.>95%.

Example 23

Preparation of (+)-(4S)-4-methyl-2-methoxy-4-phenyl-1-phenylamino-2-imidazolin-5-one Compound 503):

80 ml of methanol and then 0.74 g (0.032 mol) of sodium, cut into thin pieces, are introduced into a 250 ml, three-necked, round-bottomed flask under a dry nitrogen atmosphere. 5 g (0.016 mol) of (+)-(4S)-4-methyl-2-methylthio-4-phenyl-1-phenylamino-2-imidazolin-5-one are then added. The mixture is brought to reflux for 20 hours. The mixture is cooled to room temperature and then acidified with 0.5 ml of acetic acid. The methanol is removed by distillation under reduced pressure and the residue obtained is then taken up in 50 ml of ethyl ether, washed with 3 times 40 ml of water, dried over magnesium sulfate and then the solution is concentrated under reduced pressure. A reddish honey is obtained which is purified by chromatography on a silica column with a 70/30 heptane/ethyl acetate mixture as eluent.

2 g of (+)-(4S)-4-methyl-2-methoxy-4-phenyl-1-phenylamino-2-imidazolin-5-one are obtained in the form of a pale-pink powder melting at 132° C.; yield=42%; $[\alpha]_D^{25°\ C.}=+53.1°$ (+ or −2.4°) (c=1 in methanol); e.e.>98%.

In the same way, the following analogous compounds of formula (I"d) were obtained:

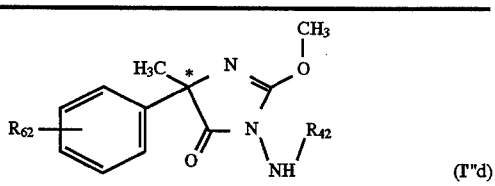

(I"d)

| Compound No. | R$_{42}$ | R$_{62}$ | $[\alpha]_D$ (c) Solvent | M.p. (°C.) | Yield (%) |
|---|---|---|---|---|---|
| 503 | Ph | H | +53° (1.0) MeOH | 132 | 42 |
| 525 | Ph | 4-F | +34° (0.5) | 129 | 66 |

-continued $$\text{(I''d)}$$

| Compound No. | $R_{42}$ | $R_{62}$ | $[\alpha]_D$ (c) Solvent | M.p. (°C.) | Yield (%) |
|---|---|---|---|---|---|
| 526 | Ph | 4-F | −33° (0.5) EtOH | 129 | 66 |
| 527 | 3-FPh | 4-F | +29° (0.5) EtOH | 130 | 43 |
| 528 | 3-FPh | 4-F | (−) | — | — |
| 529 | Ph | 4-(4-FPh)O | (+) | glass | 25 |
| 530 | Ph | 4-(4-FPh)O | −12° (0.4) EtOH | glass | 44 |

Example 24

Preparation of (+)-(2S)-2-amino-2-phenylpropionic acid (Compound 510):

22 g (0.115 mol) of (+)-(5S)-5-methyl-5-phenylhydantoin, 100 ml of water and 100 ml of 28% aqueous ammonia are introduced successively into a 1 liter autoclave. The medium is heated at 160° C. for 15 hours. After cooling to room temperature, the solution is concentrated under reduced pressure. The white solid obtained is treated with 100 ml of ethyl acetate for 2 hours and then filtered and dried under vacuum at 80° C.

10.5 g of (+)-(2S)-2-amino-2-phenylpropionic acid are collected in the form of a white powder which has a decomposition temperature of 266° C.; yield=55%; $[\alpha]_D^{27°}$ c=+71.9° (+ or −3.1°) (c=0.8 in 1N hydrochloric acid).

In the same way, the following analogous compounds of formula (XXIa) were obtained:

$$\text{(XXIa)}$$

| Compound No. | $R_{62}$ | $[\alpha]_D$ (c) Solvent | M.p. (°C.) | Yield (%) |
|---|---|---|---|---|
| 510 | H | +72° (0.8) 1N HCl | 266 | 55 |
| 531 | 4-F | (+) | — | 44 |
| 532 | 4-F | (−) | — | 92 |
| 533 | 4-(4-FPh)O | (+) | — | 87 |
| 534 | 4-(4-FPh)O | (−) | — | 76 |

Example 25 illustrates the preparation of the compounds of formula (XXVII).

Example 25

Preparation of (+)-(5S)-5-methyl-5-phenylhydantoin (Compound 535):

5.6 g (0.139 mol) of sodium hydroxide are added to a stirred suspension of 70.0 g (0.368 mol) of (5R,5S)-5-methyl-5-phenylhydantoin in 2000 ml of water. The solution obtained is brought to 40° C. and then 44.6 g (0.368 mol) of (+)-R-α-methylbenzylamine are added. The solution obtained is maintained at 50° C. for 0.75 hour and a white precipitate appears after 3 minutes. On completion of heating, the reaction medium is allowed to crystallize for 24 hours, the crystals are then filtered, washed with 70 ml of water and pulled dry under an air stream for 2 hours. There are recovered 45 g of a white solid which is added to 220 ml of 1N hydrochloric acid at 10° C. The suspension obtained is stirred for 2 hours, the crystals are then filtered, washed with 100 ml of water and pulled dry and then dried under reduced pressure at 50° C. for 15 hours. There are thus recovered 23 g (0.121 mol) of (+)-(5S)-5-methyl-5-phenylhydantoin in the form of an off-white solid melting at 242° C.; yield=66%; $[\alpha]_D^{29°}$ $^C$=+113° (c=1.0 in ethanol).

In the same way, by using (−)-S-α-methylbenzylamine, (−)-(5R)-5-methyl-5-phenylhydantoin is recovered in the form of an off-white solid melting at 248° C.; yield=54%; $[\alpha]_D^{29°}$ $^C$=+120° (c=1.0 in ethanol).

In the same way, the following analogous compounds of formula (XXVIIa) were obtained:

$$\text{(XXVIIa)}$$

| Compound No. | $R_{62}$ | $[\alpha]_D$ (c) Solvent | M.p. (°C.) | Yield (%) |
|---|---|---|---|---|
| 535 | H | +113° (1.0) EtOH | 242 | 66 |
| 536 | H | −120° (1.0) EtOH | 248 | 54 |
| 537 | 4-F | +111° (0.8) EtOH | 230 | 44 |
| 538 | 4-F | −114° (0.8) EtOH | 230 | 31 |
| 539 | 4-(4-FPh)O | +54° (0.5) EtOH | 190 | — |
| 540 | 4-(4-FPh)O | −57° (0.6) EtOH | 189 | 40 |

The Examples below illustrate the optically active derivatives of formula (I''') obtained according to Variant B of the process of preparation.

Example 26

Separation of the (+) and (−) enantiomers of the compound of the following formula (Compounds 501 and 502):

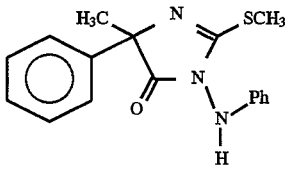

The corresponding racemic compound is prepared according to a procedure analogous to that described in Example 1 hereinabove. This racemic compound is dissolved in an eluent mixture composed of n-heptane, isopropanol and dichloromethane, in the respective portion by weight of 93, 5 and 2%.

2.3 ml of the mixture thus obtained are injected into the chiral, high performance chromatographic column with the following characteristics:

- column of Pirkle type, with a diameter of 10 mm and a length of 250 mm;
- support: 5 μm 100 angström silica containing ionic D-phenylglycine grafts.

The flow rate chosen is 10 ml/minute and the detector used is a UV detector at 250 nm. The enantiomerically pure compounds are recovered by fractionation and concentration of the pure fractions.

The physical characteristics of the enantiomers obtained, namely the melting point M.p., the optical rotation $[\alpha]_D^{20}$, measured in degrees for the compound dissolved in ethanol at a concentration of 0.5 g per 100 ml, and the retention time $t_R$, have been collated in the table below:

| Compound No. | M.p. (°C.) | $[\alpha]_D^{20}$ | $t_R$ (in minutes) |
|---|---|---|---|
| 501 | 138 | +60.7 + or − 1.3 | 5.73 |
| 502 | 138 | −59.6 + or − 0.9 | 6.55 |

Example 27

Separation of the (+) and (−) enantiomers of the compound of the following formula (Compounds 503 and 504):

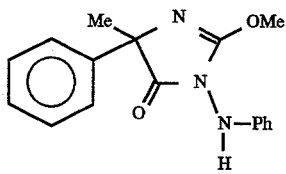

The corresponding racemic compound is prepared according to a procedure analogous to that described in Example 18 hereinabove. The corresponding (+) and (−) enantiomers (Compounds 503 and 504, respectively) are obtained by carrying out the separation in the same way as above. The volume injected into the chiral column is 1.5 ml. The optical rotation is measured after dissolving the compounds in methanol and appears with the other physical characteristics, identical to those determined above, in the table below.

| Compound No. | M.p. (°C.) | $[\alpha]_D^{20}$ | $t_R$ (in minutes) |
|---|---|---|---|
| 503 | 132 | +51.3 + or − 1.2 | 9.89 |
| 504 | 132 | −53.2 + or − 1.3 | 11.17 |

Example 28

Separation of the (+) and (−) enantiomers of the compound of the following formula (Compounds 505 and 506):

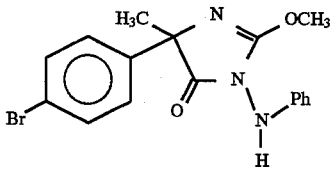

The corresponding racemic compound is prepared according to a procedure analogous to that described in Example 18 hereinabove. The corresponding (+) and (−) enantiomers (Compounds 505 and 506, respectively) are obtained by carrying out the separation in the same way as above. The results obtained are collated in the table below:

| Compound No. | M.p. (°C.) | $[\alpha]_D^{20}$ (c) Solvent | Absolute Configuration |
|---|---|---|---|
| 505 | 202 | +32.3° (c = 0.5) MeOH | S |
| 506 | 202 | 32.2° (c = 0.5) MeOH | R |

The absolute configuration of Compounds 501 to 504 was determined by chemical correlation with the absolute configuration of the corresponding α-amino acid described in the literature. The absolute configuration of Compounds 505 and 506 was determined by X-ray crystallography.

EXAMPLES OF THE ANTIFUNGAL PROPERTIES OF COMPOUNDS OF THE INVENTION

Example 29

In vitro test of compounds of formula (I):

The action of the compounds of formula (I) according to the invention is studied on the following fungi responsible for diseases of cereals and other plants:

*Fusarium oxysporum* f.sp. *melonis*

*Rhizoctonia solani* AG4

*Helminthosporium gramineum*

*Pseudocercosporella herpotrichoides*

*Alternaria alternata*

*Septoria nodorum*

*Fusarium roseum*

*Pythium rostratum*

*Pythium vexans*

Each test is carried out in the following way: a nutrient medium consisting of potato, glucose and gelose (PDA medium) is introduced in the supercooled state into a series of Petri dishes (100 ml per dish) after sterilization in an autoclave at 120° C.

While filling the dishes, an acetone solution of the active material is injected into the supercooled medium to obtain the desired final concentration.

The controls consist of Petri dishes analogous to the above which have been charged with similar quantities of a nutrient medium which does not contain active material.

After 24 hours, each dish is cultured by depositing a fragment of ground mycelium arising from a previous culture of the same fungus.

The dishes are stored for 5 days at 20° C. and the growth of the fungus in the dishes containing the active material to be tested is then compared with that of the same fungus in the dish used as the control.

For each compound tested, the degree of inhibition of the fungus studied is thus determined for a dose of 20 ppm.

The following results are then obtained:

A good activity, that is to say a degree of inhibition of the fungus of between 80% and 100%, was found for the following compounds of formula (I):

Compounds 9, 13, 16, 22, 26 and 34 for *Pythium rostratum* and *Pythium vexans*;

Compound 26 for *Fusarium oxysporum* and *Fusarium roseum*;

Compounds 11, 16, 22 and 26 for *Alternaria alternata*;

Compounds 11, 16 and 26 for *Rhizoctonia solani*;

Compounds 16 and 26 for *Pseudocercosporella herpotrichoides*;

Compounds 11, 16 and 26 for *Septoria nodorum*; and

Compounds 9, 11, 16 and 26 for *Helminthosporium gramineum*.

Example 30

In vivo test on Plasmopara viticola (grape downy mildew) of compounds of formulae (I), (I') and (I"):

An aqueous suspension of the active material to be tested is prepared, by fine milling, having the following composition:

active material: 60 mg

Tween 80 surface-active agent (oleate of polyoxyethylenated derivative of sorbitan) diluted to 10% in water: 0.3 ml volume made up to 60 ml with water.

This aqueous suspension is then diluted with water to produce the desired concentration of active material.

Vine cuttings (Vitis vinifera), Chardonnay variety, are grown in pots. When these plants are 2 months old (8–10-leaf stage, height of 10 to 15 cm), they are treated by spraying with the above aqueous suspension.

Plants used as controls are treated with an aqueous solution which does not contain the active material.

After drying for 24 hours, each plant is infected, by spraying, with an aqueous suspension of spores of *Plasmopara viticola* obtained from a 4–5 day culture, and then suspended at a concentration of 100,000 units per cm$^3$.

The infected plants are then incubated for two days at approximately 18° C. in an atmosphere saturated with moisture and then for 5 days at approximately 20°–22° C. under 90–100% relative humidity.

Reading is carried out 7 days after infecting, by comparison with the control plants.

Under these conditions, a good (at least 75%) or complete protection is observed, at a dose of 1 g/l, with the following compounds of formula (I): 1, 2, 9, 10, 12, 13, 15, 16, 18, 20, 22, 23, 24, 25, 30, 31, 34, 35, 37, 39 to 43, 45, 48, 55 to 58, 60, 62, 64, 68, 73, 75, 76, 83 to 85, 88 to 91, 93 to 98, 101 to 108.

Under these conditions, a good (at least 75%) or complete protection is also observed, at a dose of 1 g/l, with the following compounds of formula (I'): 201, 202, 203,213, 215 to 218, 220 to 222, 224, 226 to 230, 235,237 to 257, 259 to 262, 264 to 267.

Also under these conditions, a good (at least 75%) or total protection is seen at a dose of 1 g/l with the following compounds of formula (I"): 401,403 to 421,423 to 425, 427 to 481,483,484 and 486.

Example 31

In vivo test on Puccinia recondita (brown rest of wheat) of compounds of formulae (I), (I') and (I"):

An aqueous suspension of the active material m be tested is prepared, by fine milling, having the following composition:

active material: 60 mg

Tween 80 surface-active agent (oleate of polyoxyethylenated derivative of sorbitan) diluted to 10% in water: 0.3 ml volume made up to 60 ml with water.

This aqueous suspension is then diluted with water to produce the desired concentration of active material.

Wheat, in pots, sown on a 50/50 peat/pozzolana earth substrate, is treated at the 10 cm high stage by spraying the above aqueous suspension.

After 24 hours, an aqueous suspension of spores (100,000 sp/cm$^3$) of *Puccinia recondita* is sprayed on the wheat; this suspension was obtained from infected plants. The wheat is then placed for 24 hours in an incubation cell at approximately 20° C. and at 100% relative humidity, and then for 7 to 14 days at 60% relative humidity.

Monitoring of the condition of the plants is carried out between the 8th and 15th day after infection, by comparison with an untreated control.

Under these conditions, a good (at least 75%) or complete protection is observed, at a dose of 1 g/l, with the following compounds of formula (I): 2, 9, 10, 15, 18, 20 to 22, 39, 55, 57, 64, 68, 75, 83 to 85, 88 to 90, 93, 94 and 98.

Under these conditions, a good (at least 75%) or complete protection is observed, at a dose of 1 g/l, with the following compounds of formula (I'): 201, 202, 203, 208, 212, 217, 221, 222, 224, 228, 230, 235, 253, 254, 256 and 259.

Also under these conditions, good (at least 75%) or total protection is seen, at a dose of 1 g/l, with the following compounds of formula (I"): 401,404 to 410, 414, 415,419 to 421,423, 425, 427 to 429, 431 to 433,436, 437, 439, 440 to 448, 450 to 455, 457, 458, 460, 461, 463 to 467, 469, 471 to 480, 482 to 484 and 486.

Example 32

In vivo test on Phytophthora infestans (tomato late blight) of compounds of formulae (I), (I') and (I"):

An aqueous suspension of the active material to be tested is prepared, by fine milling, having the following composition:

active material: 60 mg

Tween 80 surface-active agent (oleate of polyoxyethylenated derivative of sorbitan) diluted to 10% in water: 0.3 ml volume made up to 60 ml with water.

This aqueous suspension is then diluted with water to produce the desired concentration of active material.

Tomato plants (Marmande variety) are grown in pots. When these plants are one month old (5 to 6-leaf stage, 12 to 15 cm high), they are treated by spraying the above aqueous suspension at various concentrations of the compound to be tested.

After 24 hours, each plant is infected by spraying with an aqueous suspension of spores (30,000 sp/cm$^3$) of *Phytophthora infestans*.

After this infecting, the tomato plants are incubated for 7 days at approximately 20° C. in an atmosphere saturated with moisture.

Seven days after infecting, the results obtained in the case of the plants treated with the active material to be tested are compared with those obtained in the case of the plants used as controls.

Under these conditions, a good (at least 75%) or complete protection is observed, at a dose of 1 g/l, with the following compounds of formula (I): 2, 9, 15, 30, 39, 45, 55, 68, 75, 84, 85, 90, 94, 98, 107 and 108.

Under these conditions, a good (at least 75%) or complete protection is also observed, at a dose of 1 g/l, with the following compounds of formula (I'): 201,202, 213,218, 221,224, 249, 254.

Also under these conditions, a good (at least 75%) or total protection is seen, at a dose of 1 g/l, with the following compounds of formula (I'): 401,404 to 410, 415, 418 to 421,423,428, 429, 431 to 433, 436, 437, 439, 442 to 444, 446 to 455, 457, 458, 460 to 467, 472 to 474, 481,484 and 486.

These results clearly show the good fungicidal properties of the derivatives of formulae (I), (I') and (I") according to the invention against fungal diseases of plants due to fungi belonging to the most diverse families, such as the Phycomycetes, Basidiomycetes, Ascomycetes, Adelomycetes or Fungi Imperfecti, in particular grape downy mildew, tomato late blight and brown rust of wheat.

Example 33

In vivo test on *Pyricularia oryzae* (blast disease of rice) of compounds of formula (I"):

An aqueous suspension is prepared, by fine grinding, of the active substance to be tested having the following composition:

active substance: 60 mg surface-active agent (oleate of polyoxyethylene derivative of sorbitan) diluted to 10% in water: 0.3 ml water: quantity sufficient to make 60 ml.

This aqueous suspension is then diluted with water to obtain the desired concentration of active substance.

Rice, sown in pots in a 50:50 mixture of enriched peat and pozzolana, is treated at the approximately 10 cm height stage (which corresponds to the 2-3 leaf stage) by spraying with the aqueous suspension above.

After 24 hours, an aqueous suspension of spores of *Pyricularia oryzae*, obtained from a culture of 15 days and then suspended at a rate of 100,000 units per cm$^3$, is applied to the leaves.

The rice plants are incubated for 24 hours (25° C., 100% relative humidity), then put in an observation chamber, under the same conditions, for 5 days.

Reading takes place 6 days after contamination.

Under these conditions, good (at least 75%) or total protection is seen, at a dose of 1 g/l, with the following compounds of formula (I"): 401, 404 to 407, 417, 419, 420, 423, 425,429, 431 to 433, 435, 440 to 443, 446, 447, 450, 452, 454, 455, 457, 459, 461,463 to 467, 471,472, 474, 478, 482, 484 and 485.

Example 34

In vivo test on *Septoria tritici* (leaf spot of wheat) of compounds of formula (I"):

An aqueous suspension, of concentration 1 g/l, of the active substance tested is obtained by grinding 60 mg of the latter in the following mixture:

acetone: 5 ml surface-active agent (oleate of polyoxyethylene derivative of sorbitan) diluted in 10%: 0.3 ml, then the volume is adjusted to 60 ml with water.

This aqueous suspension is then diluted with water to obtain the desired concentration of active substance.

Wheat plants (Darius variety), sown on a 50:50 peat-pozzolana substrate and grown under glass at a temperature of 10°–12° C., are treated at the 1 leaf stage (height of approximately 10 cm) by spraying with the suspension of active substance described above.

Some plants, used as controls, are treated by spraying with an aqueous solution which does not contain the active substance.

24 hours after treatment, the plants are contaminated by spraying with an aqueous suspension of spores (500,000 spores/ml) of *Septoria tritici* collected in a 7 day-old culture.

After contamination, the plants are placed in a humid atmosphere at 18° C. Marking is carried out 20 days after contamination in comparison with the control plants.

Under these conditions, good (at least 75%) or total protection is seen, at a dose of 1 g/l, with the following compounds of formula (I"): 401,404 to 406, 409, 419, 420, 423, 432, 433,435 to 437, 440, 442 to 445, 447, 448, 450, 452, 454, 455, 457, 458, 460, 462 to 464, 466, 467, 471 to 480, 483,484 and 486.

These results clearly show the good fungicidal properties of the derivatives of formula (I") according to the invention against additional fungal diseases of plants, in particular leaf spot of wheat and also blast disease of rice.

The following Examples illustrate the fungicidal properties of Compounds 501 to 506, 511 to 514 and 525 to 528 of formula (I'") according to the invention. In these Examples, the racemic modification corresponding to enantiomeric Compounds 501 and 502 is recorded as 501+502. Likewise, the racemic modification corresponding to Compounds 503 and 504 is recorded as 503+504. More generally, the racemic modification corresponding to enantiomeric Compounds n and n+1 is recorded as n+(n+1).

Example 35

In vivo comparative test on *Puccinia recondita* (brown rust of wheat) of compounds of formula (I'"):

An aqueous suspension of the active material to be tested is prepared, by fine milling, having the following composition:

active material: 60 mg

Tween 80 surface-active agent (oleate of polycondensate of ethylene oxide with sorbitan) diluted to 10% in water: 0.3 ml volume made up to 60 ml with water.

The active material to be tested is either one of the two enantiomers of formula (I'") according to the invention or the corresponding racemic modification.

This aqueous suspension is then diluted with water to produce the desired concentration of active material.

Wheat of the Talent variety, in pots, sown on a 50/50 peat/pozzolana earth substrate, is treated at the 10 cm high stage by spraying the above aqueous suspension.

After 24 hours, an aqueous suspension of spores (100,000 sp/cm$^3$) of *Puccinia recondita* is sprayed on the wheat; this suspension was obtained from infected seedlings. The wheat is then placed for 24 hours in an incubation cell at approximately 20° C. and at 100% relative humidity, and then for 7 to 14 days at 60% relative humidity.

Monitoring of the condition of the seedlings is carried out between the 8th and 151th day after infection, by comparison with an untreated control. The concentration of active material tested, IC$_{75}$ (expressed in ppm), at which 75% inhibition of the disease is observed, is then determined.

The results are collated in the following table:

| Compound No. | IC$_{75}$ (ppm) |
| --- | --- |
| 501 + 502 | 330 |
| 501 | 37 |
| 502 | >1000 |
| 503 + 504 | 330 |
| 503 | 110 |
| 504 | >1000 |
| 505 + 506 | 330 |
| 505 | 110–330 |
| 506 | >1000 |
| 511 + 512 | 37–110 |
| 511 | 12–37 |
| 512 | — |
| 513 + 514 | 37 |
| 513 | 12 |
| 514 | — |
| 525 + 526 | 12 |

| Compound No. | IC$_{75}$ (ppm) |
| --- | --- |
| 525 | — |
| 526 | >1000 |
| 527 + 528 | 37 |
| 527 | 4 |
| 528 | — |

Example 36

In vivo comparative test on *Phytophthora infestans* (tomato late blight) of compounds of formula (I'''):

An aqueous suspension of the active material to be tested is prepared, by fine milling, having the following composition:

active material: 60 mg

Tween 80 surface-active agent (oleate of polycondensate of ethylene oxide with sorbitan) diluted to 10% in water: 0.3 ml volume made up to 60 ml with water.

The active material to be tested is chosen from the same compounds as in the preceding example.

This aqueous suspension is then diluted with water to produce the desired concentration of active material.

Tomato seedlings (Marmande variety) are grown in pots. When these seedlings are one month old (5 to 6-leaf stage, 12 to 15 cm high), they are treated by spraying the above aqueous suspension at various concentrations of the compound to be tested.

After 24 hours, each seedling is infected by spraying with an aqueous suspension of spores (30,000 sp/cm$^3$) of *Phytophthora infestans*.

After this infecting, the tomato seedings are incubated for 7 days at approximately 20° C. in an atmosphere sainted with moisture.

Seven days after infecting, the results obtained in the case of the seedlings treated with the active material to be tested are compared with those obtained in the ease of the seedlings used as controls. The concentration of active material tested, IC$_{75}$ (expressed in ppm), at which 75% inhibition of the disease is observed, is then determined.

The results are collated in the following table:

| Compound No. | IC$_{75}$ (ppm) |
| --- | --- |
| 501 + 502 | 110 |
| 501 | 37 |
| 502 | >1000 |
| 503 + 504 | 330 |
| 503 | 110 |
| 504 | >1000 |
| 505 + 506 | >1000 |
| 505 | 37 |
| 506 | >1000 |
| 511 + 512 | 110 |
| 511 | 12–37 |
| 512 | — |
| 513 + 514 | 110 |
| 513 | 37 |
| 514 | — |
| 525 + 526 | 110 |
| 525 | 37 |
| 526 | >1000 |
| 527 + 528 | 37 |
| 527 | 4–12 |
| 528 | — |

In one preferred aspect, the present invention also relates to the compositions for protecting plants against fungal diseases, comprising, in combination with one or more solid or liquid vehicles which are acceptable in agriculture and/or surface-active agents which are also acceptable in agriculture, one (or a number of) active material which is a compound of formula (I'''). Preferably, the active material of formula (I''') consists of the optically pure enantiomer which has the greater fungicidal activity, or contains the enantiomer having the greater fungicidal activity in greatly enriched form (as defined hereinabove).

In fact, generally speaking, for their practical use the compounds according to the invention, i.e. the compounds of formulae (I), (I'), (I'') and (I'''), are rarely used on their own. Most often these compounds form part of compositions. These compositions, which can be used as fungicidal agents, contain, as active material or active substance a compound according to the invention as described above as a mixture with solid or liquid vehicles or supports which are acceptable in agriculture and surface-active agents which are also acceptable in agriculture. In particular, the customary inert vehicles or supports and the customary surface-active agents can be used. These compositions also form part of the invention.

These compositions can also contain all kinds of other ingredients such as, for example, protective colloids, adhesives, thickening agents, thixotropic agents, penetration agents, stabilizing agents, sequestering agents and the like. More generally, the compounds used in the invention can be used in combination with any of the solid or liquid additives which correspond to the usual formulating techniques.

Generally, the compositions according to the invention usually contain approximately 0.05 to 95% Coy weight) of a compound according to the invention, i.e. a compound of formula (I), (I'), (I'') or (I''') (subsequently called "active material" or "active substance"), one or more solid or liquid vehicles or supports and, optionally, one or more surface-active agents.

The term "vehicle" or "support", in the present account, means a natural or synthetic, organic or inorganic material with which the compound is combined in order to facilitate its application to the plant, to seeds or to the soil. This vehicle is therefore generally inert and it has to be acceptable in agriculture, especially m the treated plant. The vehicle can be solid (clays, natural or synthetic silicates, silica, resins, waxes, solid fertilizers, and the like) or liquid (water, alcohols, especially butanol, and the like).

The surface-active agent can be an emulsifying, dispersing or wetting agent of ionic or nonionic type or a mixture of such surface-active agents. There may be cited, for example, salts of poly(acrylic acids), salts of lignosulfonic acids, salts of phenolsulfonic or naphthalenesulfonic acids, polycondensates of ethylene oxide with fatty alcohols or fatty acids or fatty amines, substituted phenols (especially alkylphenols or arylphenols), salts of esters of sulfosuccinic acids, derivatives of murine (especially alkyltaurates), phosphoric esters of polycondensates of ethylene oxide with alcohols or phenols, esters of fatty acids and of polyols, and the derivatives of the above compounds having sulfate, sulfonate or phosphate functional groups. The presence of at least one surface-active agent is generally indispensable where the compound and/or the inert vehicle are/is not soluble in water and where the vector agent of the application is water.

Thus, the compositions for agricultural use according to the invention can contain the active materials according to the invention within very wide limits, ranging from 0.05% to 95% (by weight). Their surface-active agent content is advantageously between 5% and 40% by weight.

These compositions according to the invention are themselves in fairly diverse, solid or liquid forms.

There may be mentioned, as solid composition forms, powders for dusting (containing the compound at a content of up to 100%) and granules, especially those obtained by extrusion, by compacting, by impregnation of a granulated vehicle, or by granulation from a powder (the content of the compound in these granules being between 0.5 and 80% for the latter cases), tablets/pills or effervescent tablets.

The compounds of formulae (I), (I'), (I'') and (I''') can also be used in the form of powders for dusting; it is also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

As composition forms which are liquid or intended to constitute liquid compositions during application, there my be mentioned solutions, in particular water-soluble concentrates, emulsifiable concentrates, emulsions, suspension concentrates, aerosols, wettable powders (or sprayable powders), pastes or gels.

The emulsifiable or soluble concentrates most often comprise 10 to 80% of active material, while the ready-to-apply solutions or emulsions contain 0.001 to 20% of active material.

In addition to the solvent, the emulsifiable concentrates can contain, when this is necessary, 2 to 20% of suitable additives such as the stabilizing agents, surface-active agents, penetration agents, corrosion inhibitors, dyes or adhesives mentioned above.

It is possible, by diluting these concentrates with water, to obtain emulsions of any desired concentration which are particularly suitable for application to crops.

By way of example, the composition of several emulsifiable concentrates will now be given:

Example EC1

| active material | 400 g/l |
|---|---|
| alkaline dodecylbenzenesulfonate | 24 g/l |
| condensate of 10 molecules of ethylene oxide with nonylphenol | 16 g/l |
| cyclohexanone | 200 g/l |
| aromatic solvent | q.s. 1 liter |

According to another emulsifiable concentrate formula, there are used:

Example EC2

| active material | 250 g |
|---|---|
| epoxidized vegetable oil | 25 g |
| mixture of alkylarylsulfonate and of ether of polyglycol and fatty alcohols | 100 g |
| dimethylformamide | 50 g |
| xylene | 575 g |

The suspension concentrates, which can also be applied by spraying, are prepared so as to produce a stable fluid product which does not settle out and they generally contain from 10 to 75% of active material, from 0.5 to 15% of surface-active agents, from 0.1 to 10% of thixotropic agents, from 0 to 10% of suitable additives, such as antifoaming agents, corrosion inhibitors, stabilizing agents, penetration agents and adhesives and, as vehicle or support, water or an organic liquid in which the active tutorial has little or no solubility: certain solid organic materials or inorganic salts can be dissolved in the vehicle to help in preventing sedimentation or as antifreeze for the water.

By way of example, the composition of a suspension concentrate will now be given:

Example SC1

| active material | 500 g |
|---|---|
| polycondensate of ethylene oxide with tristyrylphenyl phosphate | 50 g |
| polycondensate of ethylene oxide with alkylphenol | 50 g |
| sodium polycarboxylate | 20 g |
| ethylene glycol | 50 g |
| organopolysiloxane oil (antifoam) | 1 g |
| polysaccharide | 1.5 g |
| water | 316.5 g |

The wettable powders (or sprayable powders) are generally prepared so that they contain 20 to 95% of active material, and they generally contain, in addition to the solid vehicle, from 0 to 30% of a wetting agent, from 3 to 20% of a dispersing agent and, when necessary, from 0.1 to 10% of one or more stabilizing agents and/or other additives, such as penetration agents, adhesives, or anticaking agents, dyes, and the like.

In order to obtain the sprayable powders or wettable powders, the active materials are intimately mixed in suitable mixers with the additional substances and the mixture is milled in mills or other suitable grinders. Sprayable powders are thereby obtained whose wettability and suspensibility are advantageous; they can be suspended in water at any desired concentration and these suspensions can be used very advantageously, in particular, for application to plant leaves.

Instead of wettable powders, it is possible to produce pastes. The conditions and method for producing and using these pastes are similar to those for the wettable powders or sprayable powders.

By way of example, various wettable powder (or sprayable powder) compositions will now be given:

Example WP1

| active material | 50% |
|---|---|
| condensate of ethylene oxide with fatty alcohol (wetting agent) | 2.5% |
| condensate of ethylene oxide with phenylethylphenol (dispersing agent) | 5% |
| chalk (inert vehicle) | 42.5% |

Example WP2

| active material | 10% |
|---|---|
| condensate of 8 to 10 mol of ethylene oxide with $C_{13}$ branched-type synthetic oxo alcohol (wetting agent) | 0.75% |
| neutral calcium lignosulfonate (dispersing agent) | 12% |
| calcium carbonate (inert filler) | q.s. 100% |

Example WP3

This wettable powder contains the same ingredients as in the above Example, in the proportions below:

| | |
|---|---|
| active material | 75% |
| wetting agent | 1.50% |
| dispersing agent | 8% |
| calcium carbonate (inert filler) | q.s. 100% |

Example WP4

| | |
|---|---|
| active material | 90% |
| condensate of ethylene oxide with fatty alcohol (wetting agent) | 4% |
| condensate of ethylene oxide with phenylethylphenol (dispersing agent) | 6% |

Example WP5

| | |
|---|---|
| active material | 50% |
| mixture of anionic and nonionic surface-active agents (wetting agent) | 2.5% |
| sodium lignosulfonate (dispersing agent) | 5% |
| kaolin clay (inert vehicle) | 42.5% |

The aqueous dispersions and emulsions, for example, the compositions obtained by diluting a wettable powder or an emulsifiable concentrate according to the invention using water, are included within the general scope of the present invention. The emulsions can be of water-in-oil or oil-in-water type and they have a thick consistency like that of a "mayonnaise".

The compounds according to the invention can be formulated in the form of water-dispersible granules also included in the scope of the invention.

These dispersible granules, with an apparent density generally between approximately 0.3 and 0.6, have a particle size generally between approximately 150 and 2,000 and preferably between 300 and 1,500 microns.

The active material content of these granules is generally between approximately 1% and 90%, and preferably between 25% and 90%.

The remainder of the granule is essentially composed of a solid filler and optionally of surface-active adjuvants which confer water-dispersibility properties on the granule. These granules can be essentially of two distinct types depending upon whether the flier used is soluble or insoluble in water. When the filler is water-soluble, it can be inorganic or, preferably, organic. Excellent results have been obtained with urea. In the case of an insoluble flier, the latter is preferably inorganic, such as, for example, kaolin or bentonite. It is then advantageously accompanied by surface-active agents (at an amount of 2 to 20% by weight of the granule) of which more than half consists, for example, of at least one essentially anionic dispersing agent such as an alkali metal or alkaline-earth metal polynaphthalene sulfonate or an alkali metal or alkaline-earth metal lignosulfonate, the remainder consisting of nonionic or anionic wetting agents such as an alkali metal or alkaline-earth metal alkylnaphthalene sulfonate.

Moreover, although this is not indispensable, it is possible to add other adjuvants such as anti-foaming agents.

The granule according to the invention can be prepared by mixing the required ingredients and then granulating according to several techniques known per se (pelletizer, fluid bed, atomizer, extrusion, and the like). Generally, the preparation is completed by crushing followed by sieving to the particle size chosen within the above-mentioned limits. It is alternatively possible to use granules obtained as above and then impregnated with a composition containing the active material.

Preferably, it is obtained by extrusion, the preparation being carried out as shown in the Examples below.

Example DG1

This is an example of the preparation of dispersible granules.

90% by weight of active material and 10% of urea in the pearl form are mixed in a mixer. The mixture is then milled in a pin mill or toothed roll crusher. A powder is obtained which is moistened with approximately 8% by weight of water. The damp powder is extruded in a perforated-cylinder extruder. A granule is obtained which is dried and then crushed and sieved so as to retain only the granules with a size between 150 and 2,000 microns, respectively.

Example DG2

This is another example of the preparation of dispersible granules.

The following constituents are mixed in a mixer:

| | |
|---|---|
| active material | 75% |
| wetting agent (sodium alkylnaphthalene sulfonate) | 2% |
| dispersing agent (sodium polynaphthalene sulfonate) | 8% |
| water-insoluble inert filler (kaolin) | 15% |

This mixture is granulated in a fluid bed, in the presence of water, and is then dried, crushed and sieved so as to produce granules of between 0.15 and 0.80 mm in size.

These granules can be used alone or in solution or dispersion in water so as to produce the required dose. They can also be used to prepare combinations with other active materials, especially fungicides, the latter being in the form of wettable powders or of granules or aqueous suspensions.

As regards the compositions which are suitable for storing and transporting, they more advantageously contain from 0.5 to 95% (by weight) of active substance in the ease of compounds of formulae (I) and (I'') and from 0.05 to 95% Coy weight) of active substance in the case of compounds of formulae (I') and (I''').

Another subject of the invention is a process for the treatment of crops affected by or capable of being affected by fungal diseases, characterized in that an effective amount of a compound of formulae (I), (I') or (I'') or an optically active compound of formula (I''') is applied preventatively or curatively m the plants or their grog site. As with the fungicidal compositions of the invention, when the active material is a compound of formula (I'''), it is preferable in use that the compound be the optically pure enantiomer which has the greater fungicidal activity of the pair or that the compound of formula (I''') contain in greatly enriched form the enantiomer having the greater fungicidal activity of the pair.

The compounds of formulae (I), (I'), (I'') and (I''') are advantageously applied at doses of 0.005 to 5 kg/ha, and more specifically of 0.01 to 1 kg/ha.

While the invention has been described in tens of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A compound having the formula:

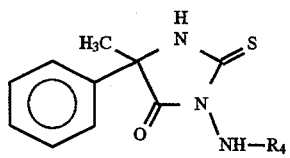

wherein $R_4$ is:

alkyl having 1 to 6 carbon atoms;

alkoxyalkyl, alkylthioalkyl, haloalkyl, cyanoalkyl, thiocyanatoalkyl, alkenyl or alkynyl having 2 to 6 carbon atoms;

dialkylaminoalkyl, alkoxycarbonylalkyl or N-alkylcarbamoylalkyl having 3 to 6 carbon atoms;

N,N-dialkylcarbamoylalkyl having 4 to 8 carbon atoms;

aryl selected from the group consisting of phenyl, naphthyl, thienyl, furyl, pyridyl, pyrimidyl, pyridazinyl, pyrazinyl, benzothienyl, benzofuryl, quinolyl, isoquinolyl and methylenedioxyphenyl, each of which is unsubstituted or is substituted by 1 to 3 $R_7$ substituents wherein $R_7$ is as defined below;

arylalkyl, aryloxyalkyl, arylthioalkyl or arylsulfonylalkyl, wherein alkyl has 1 to 6 carbon atoms and aryl is selected from the group consisting of phenyl, naphthyl, thienyl, furyl, pyridyl, pyrimidyl, pyridazinyl, pyrazinyl, benzothienyl, benzofuryl, quinolyl isoquinolyl and methylenedioxyphenyl, each of which is unsubstituted or is substituted by 1 to 3 $R_7$ substituents wherein $R_7$ is as defined below;

amino, disubstituted by two identical or different substituents selected from the group consisting of:

alkyl having 1 to 6 carbon atoms;

alkoxyalkyl, alkenyl and alkynyl having 3 to 6 carbon atoms;

cycloalkyl having 3 to 7 carbon atoms;

arylalkyl as defined above for $R_4$, phenyl and naphthyl, each of which is unsubstituted or is substituted by 1 to 3 $R_7$ substituents wherein $R_7$ is as defined below; and thienylmethyl and furfuryl; or pyrrolidino, piperidino, morpholino or piperazino, each of which is unsubstituted or is substituted by alkyl having 1 to 3 carbon atoms; and $R_7$ is:

halogen;

alkyl, haloalkyl, alkoxy, haloalkoxy, alkylthio, haloalkylthio or alkylsulfonyl having 1 to 6 carbon atoms;

cycloalkyl, halocycloalkyl, alkenyloxy, alkynyloxy, alkenylthio or alkynylthio having 3 to 6 carbon atoms;

nitro or cyano;

amino, which is unsubstituted or is substituted by 1 or 2 substituents selected from the group consisting of alkyl and acyl having 1 to 6 carbon atoms and alkoxycarbonyl having 2 to 6 carbon atoms; or phenyl, phenoxy or pyridyloxy, each of which is unsubstituted or is substituted by 1 to 3 substituents selected from the group consisting of halogen and alkyl, haloalkyl, alkoxy, haloalkoxy, alkylthio, haloalkylthio and alkylsulfonyl having 1 to 6 carbon atoms.

2. The compound according to claim 1, wherein $R_4$ is phenyl, m-tolyl, p-tolyl, 4-fluorophenyl, o-tolyl, 3-chlorophenyl, 4-chlorophenyl, 2-chlorophenyl, 4-methoxyphenyl or 2-methoxyphenyl.

3. The compound according to claim 2, wherein $R_4$ is phenyl.

* * * * *